(12) United States Patent
Byers et al.

(10) Patent No.: US 9,199,918 B2
(45) Date of Patent: Dec. 1, 2015

(54) SMALL MOLECULE INHIBITORS OF AGBL2

(75) Inventors: Stephen W. Byers, Takoma Park, MD (US); Sivanesan Dakshanamurthy, Herndon, VA (US); Ziad Sahab, Fairfax, VA (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 13/985,544

(22) PCT Filed: Feb. 14, 2012

(86) PCT No.: PCT/US2012/025069
§ 371 (c)(1),
(2), (4) Date: Aug. 14, 2013

(87) PCT Pub. No.: WO2012/112567
PCT Pub. Date: Aug. 23, 2012

(65) Prior Publication Data
US 2013/0331328 A1 Dec. 12, 2013

Related U.S. Application Data

(60) Provisional application No. 61/443,069, filed on Feb. 15, 2011.

(51) Int. Cl.

| | |
|---|---|
| *C07C 233/65* | (2006.01) |
| *A61K 31/166* | (2006.01) |
| *C07C 235/84* | (2006.01) |
| *C07D 213/56* | (2006.01) |
| *C07D 233/90* | (2006.01) |
| *C07D 307/68* | (2006.01) |
| *C07D 417/12* | (2006.01) |
| *C07C 233/75* | (2006.01) |
| *C07C 237/12* | (2006.01) |
| *A61K 31/196* | (2006.01) |
| *A61K 31/341* | (2006.01) |
| *A61K 31/357* | (2006.01) |
| *A61K 31/4155* | (2006.01) |
| *A61K 31/4178* | (2006.01) |
| *A61K 31/4406* | (2006.01) |
| *A61K 31/4436* | (2006.01) |
| *A61K 38/05* | (2006.01) |
| *A61K 45/06* | (2006.01) |
| *C07D 307/66* | (2006.01) |
| *C07D 317/46* | (2006.01) |
| *C07D 403/04* | (2006.01) |
| *C07D 409/14* | (2006.01) |
| *C07K 5/065* | (2006.01) |

(52) U.S. Cl.
CPC ............ *C07C 235/84* (2013.01); *A61K 31/196* (2013.01); *A61K 31/341* (2013.01); *A61K 31/357* (2013.01); *A61K 31/4155* (2013.01); *A61K 31/4178* (2013.01); *A61K 31/4406* (2013.01); *A61K 31/4436* (2013.01); *A61K 38/05* (2013.01); *A61K 45/06* (2013.01); *C07C 233/65* (2013.01); *C07C 233/75* (2013.01); *C07C 237/12* (2013.01); *C07D 213/56* (2013.01); *C07D 233/90* (2013.01); *C07D 307/66* (2013.01); *C07D 307/68* (2013.01); *C07D 317/46* (2013.01); *C07D 403/04* (2013.01); *C07D 409/14* (2013.01); *C07D 417/12* (2013.01); *C07K 5/06078* (2013.01)

(58) Field of Classification Search
None
See application file for complete search history.

(56) References Cited

U.S. PATENT DOCUMENTS

| 5,962,473 A | 10/1999 | Johnson et al. |
|---|---|---|
| 2005/0009876 A1 | 1/2005 | Bhagwat et al. |

FOREIGN PATENT DOCUMENTS

| EP | 2003129 | 12/2008 |
|---|---|---|
| WO | 9730034 | 8/1997 |
| WO | WO 0020358 A2 * | 4/2000 |
| WO | WO 0153274 A1 * | 7/2001 |
| WO | 03099811 | 12/2003 |
| WO | 2005058837 | 6/2005 |
| WO | 2005080367 | 9/2005 |
| WO | 2007117465 | 10/2007 |
| WO | 2008005651 | 1/2008 |
| WO | 2008112217 | 9/2008 |

OTHER PUBLICATIONS

Wu et al., Toxicology, 236, pp. 1-6, 2007.*
Hadden et al, Bioorganic & Medicinal Chemistry Letters (2007), 17(18), 5063-5067.*
Aagaard et al., Wells CA et al. An inflammatory role for the mammalian carboxypeptidase inhibitor latexin: relationship to cystatins and the tumor suppressor TIG1, Structure, vol. 13, No. 2, 2005, pp. 309-317.
Ann et al., Serum vitamin D concentration and prostate cancer risk: a nested case-control study, Journal of the National Cancer Institute, vol. 100, 2008, pp. 796-804.
Akhmanova et al., Tracking the ends: a dynamic protein network controls the fate of microtubule tips, Nature Reviews: Molecular Cell Biology, vol. 9, 2008, pp. 309-322.
Ambrosini et al., Fruit, vegetable, vitamin A intakes, and prostate cancer risk, Prostate Cancer & Prostatic Diseases, vol. 11, 2008, pp. 61-66.
Andreasen et al., Improved microRNA quantification in total RNA from clinical samples, Methods, vol. 50, 2010, pp. S6-S9.
Angers et al., The KLHL12-Cullin-3 ubiquitin ligase negatively regulates the Wnt-beta-catenin pathway by targeting Dishevelled for degradation, Nature Cell Biology, vol. 8, 2006, pp. 348-357.
Arimatsu, Early patterning of the rat cerebral wall for regional organization of a neuronal population expressing latexin, Developmental Brain Research, vol. 106, No. 1-2, 1998, pp. 71-78.
Arimatsu, Latexin: a molecular marker for regional specification in the neocortex, Neuroscience Research, vol. 20, 1994, pp. 131-135.
Armas et al., Ultraviolet-B radiation increases serum 25-hydroxyvitamin D levels: the effect of UVB dose and skin color, Journal of the American Academy of Dermatology, vol. 57, No. 4, 2007, pp. 588-593.

(Continued)

*Primary Examiner* — Zinna Northington Davis
(74) *Attorney, Agent, or Firm* — Kilpatrick Townsend & Stockton, LLP

(57) ABSTRACT

Small molecule inhibitors of AGBL2 are provided, as well as methods of using the inhibitors to treat or prevent cancer and neurologic disorders.

6 Claims, 6 Drawing Sheets

(56) References Cited

OTHER PUBLICATIONS

Ballew, Serum retinol distributions in residents of the United States: third National Health and Nutrition Examination Survey, 1988-1994, American Society for Clinical Nutrition, vol. 73, 2001, pp. 586-593.
Banerjee et al., Antiproliferative role of vitamin D and its analogs—a brief overview, Molecular and Cellular Biochemistry, vol. 253, 2003, pp. 247-254.
Beilby et al., Serum levels of folate, lycopene, beta-carotene, retinol and vitamin E and prostate cancer risk, European Journal of Clinical Nutrition, vol. 64, 2010, pp. 1235-1238.
Berezniuk et al., CCP1/Nna1 functions in protein turnover in mouse brain: Implications for cell death in Purkinje cell degeneration mice, The FASEB Journal, vol. 24, No. 6, 2010, pp. 1813-1823.
Betel et al., The microRNA.org resource: targets and expression, Nucleic Acids Research, vol. 36, 2008, pp. D149-D153.
Calvo et al., Vitamin D fortification in the United States and Canada: current status and data needs, The American Journal of Clinical Nutrition, vol. 80, 2004, pp. 1710S-1716S.
Camacho et al., Regulation of vitamin D production is independent of skin color, Journal of Investigative Dermatology, vol. 130, 2010, p. 330.
Chakrabarti et al., The Purkinje cell degeneration 5J mutation is a single amino acid insertion that destabilizes Nna1 protein, Mammalian Genome, vol. 17, No. 2, 2006, pp. 103-110.
Colli et al., Chemoprevention of prostate cancer: what can be recommended to patients?, Current Urology Reports, vol. 10, No. 3, 2009, pp. 165-171.
Cowell et al., Inactivation of LGI1 expression accompanies early stage hyperplasia of prostate epithelium in the TRAMP murine model of prostate cancer, Experimental and Molecular Pathology, vol. 88, No. 1, 2010, pp. 77-81.
Donkena et al., Vitamins and prostate cancer risk, Molecules, vol. 15, 2010, pp. 1762-1783.
Easwaran et al., The ubiquitin-proteasome pathway and serine kinase activity modulate adenomatous polyposis coli protein-mediated regulation of beta-catenin-lymphocyte enhancer-binding factor signaling, Journal of Biological Chemistry, vol. 274, No., 1999, pp. 16641-16645.
El-Araby et al., Solid-Phase Synthesis of an Alkylaminobenzanilide Library, Journal of Combinatorial Chemistry, vol. 6, No. 5, 2004, pp. 789-795.
Ellinger et al., CpG Island hypermethylation in cell-free serum DNA identifies patients with localized prostate cancer, Prostate, vol. 68, 2008, pp. 42-49.
Erck et al., A vital role of tubulin-tyrosine-ligase for neuronal organization, PNAS, vol. 102, No. 22, 2005, pp. 7853-7858.
Fernandez-Gonzalez et al., Purkinje cell degeneration (pcd) phenotypes caused by mutations in the axotomy-induced gene, Nna1, Science, vol. 295, No. 5561, 2002, pp. 1904-1906.
Fonrose et al., Parthenolide inhibits tubulin carboxypeptidase activity, Cancer Research, vol. 67, 2007, pp. 3371-3378.
Freemantle et al., Retinoids in cancer therapy and chemoprevention: promise meets resistanc, Oncogene, vol. 22, 2003, pp. 7305-7315.
Friedman et al., Most mammalian mRNAs are conserved targets of microRNAs, Genome Research, vol. 19, 2009, pp. 92-105.
Fujiwara et al., Cytokinesis failure generating tetraploids promotes tumorigenesis in p53-null cells, Nature, vol. 437, 2005, pp. 1043-1047.
Fukushima et al., Post-translational modifications of tubulin in the nervous system, Journal of Neurochemistry, vol. 109, No. 3, 2009, pp. 683-693.
Furusato et al., Mapping of TMPRSS2-ERG fusions in the context of multi-focal prostate cancer, Modern Pathology, vol. 21, 2008, pp. 67-75.
Gill et al., Association of selenium, tocopherols, carotenoids, retinol, and 15-isoprostane F(2t) in serum or urine with prostate cancer risk: the multiethnic cohort, Cancer Causes & Control, vol. 20, 2009, pp. 1161-1171.
Giovannucci, Strengths and limitations of current epidemiologic studies: vitamin D as a modifier of colon and prostate cancer risk, Nutrition Reviews, vol. 65, 2007, pp. S77-S79.
Gocek et al., Vitamin D and differentiation in cancer, Critical Reviews in Clinical Laboratory Sciences, vol. 46, 2009, pp. 190-209.
Griffiths-Jones, miRBase: microRNA sequences and annotation, Current Protocols in Bioinformatics, Chpt. 12, Unit 10, 2010.
Griffiths-Jones, The microRNA Registry, Nucleic Acids Research, vol. 32, 2004, pp. D109-D111.
Gu et al., Laminin-10/11 and fibronectin differentially regulate integrin-dependent Rho and Rac activation via p130(Cas)-CrkII-DOCK180 pathway, Journal of Biological Chemistry, vol. 276, No. 29, 2001, pp. 27090-27097.
Gundersen et al., Distribution of tyrosinated and nontyrosinated alpha-tubulin during mitosis, Journal of Cell Biology, vol. 102, 1986, pp. 1118-1126.
Gupta et al., Vitamin D and prostate cancer risk: a review of the epidemiological literature, Prostate Cancer and Prostatic Diseases, vol. 12, 2009, pp. 215-226.
Hall, Rarresl regulation of alpha-tubulin tyrosination, cytokinesis and vertebrate embryonic development, Georgetown University, Retrieved from the Internet: URL: http://search.proquest.com/docview/304887871, 2009, 180 pages.
Harris, Vitamin D and African Americans, Journal of Nutrition, vol. 136, 2006, pp. 1126-1129.
Honnappa et al., Key interaction modes of dynamic +TIP networks, Mollecular Cell, vol. 23, 2006, pp. 663-671.
Ingraham et al., Molecular basis of the potential of vitamin D to prevent cancer, Current Medical Research and Opinion, vol. 24, No. 1, 2008, pp. 139-149.
Jemal et al., Cancer statistics, 2010, CA: A Cancer Journal for Clinicians, vol. 60, No. 5, Sep./Oct. 2010, pp. 277-300.
Ji et al., Eukaryotic initiation factor 6 selectively regulates Wnt signaling and beta-catenin protein synthesis, Oncogene, vol. 27, 2008, pp. 755-762.
Jing et al., Tazarotene-induced gene 1 (TIG1) expression in prostate carcinomas and its relationship to tumorigenicity, Journal of the National Cancer Institute, vol. 94, No. 7, 2002, pp. 482-490.
Kalinina et al., A novel subfamily of mouse cytosolic carboxypeptidases, FASEB J., vol. 21, No. 3, 2007, pp. 836-850.
Kant et al., Ethnic and socioeconomic differences in variability in nutritional biomarkers, American Society for Clinical Nutrition, vol. 87, 2008, pp. 1464-1471.
Key et al., Plasma carotenoids, retinol, and tocopherols and the risk of prostate cancer in the European Prospective Investigation into Cancer and Nutrition study, Am. J. Clin. Nutr., vol. 86, 2007, pp. 672-681.
Khawaja et al., Enhanced stability of microtubules enriched in detyrosinated tubulin is not a direct function of detyrosination level, The Journal of Cell Biology, vol. 10, Jan. 1988, pp. 141-149.
Konishi et al., Tubulin tyrosination navigates the kinesin-1 motor domain to axons, Nature Neuroscience, vol. 12, No. 5, May 2009, pp. 559-567.
Kroh et al., Analysis of circulating microRNA biomarkers in plasma and serum using quantitative reverse transcription-PCR (qRT-PCR), Methods, vol. 50, 2010, pp. 298-301.
Kwok et al., Role of the RARRES1 gene in nasopharyngeal carcinoma, Cancer Genetics and Cytogenetics, vol. 194, Issue 1, Oct. 1, 2009, pp. 58-64.
Lafanechère et al., Suppression of tubulin tyrosine ligase during tumor growth, Journal of Cell Science, vol. 111, 1998, pp. 171-181.
Lafanechère et al., The third tubulin pool, Neurochemical Research, vol. 25, No. 1, 2000, pp. 11-18.
Lee et al., Epigenetic inactivation of retinoid X receptor genes in non-small cell lung cancer and the relationship with clinicopathologic features, Cancer Genet.Cytogenet, vol. 197, No. 1, 2010, pp. 39-45.
Lee et al., Evolution and expression of chimeric POTE-actin genes in the human genome, Proceedings of the National Academy of Sciences, U.S A, vol. 103, No. 47, Nov. 21, 2006, pp. 17885-17890.
Li et al., Hypermethylation in promoter region of retinoic acid receptor-beta gene and immunohistochemical findings on retinoic acid receptors in carcinogenesis of endometrium, Cancer Lett, vol. 219, No. 1, Feb. 28, 2005, pp. 33-40.

(56) References Cited

OTHER PUBLICATIONS

Liang et al., Aging stem cells, latexin and longevity, Experimental Cell Research, vol. 314, No. 9, Jun. 10, 2008, pp. 1962-1972.
Liang et al., The quantitative trait gene latexin influences the size of the hematopoietic stem cell population in mice, Nature Genetics, vol. 39, No. 2, Feb. 2007, pp. 178-188.
Lin et al., MicroRNA-143 as a tumor suppressor for bladder cancer, Journal of Urology, vol. 181, No. 3, Mar. 2009, pp. 1372-1380.
Loebinger et al., Mesenchymal Stem Cell Delivery of Trail Can Eliminate Metastatic Cancer, Cancer Research, vol. 69, No. 10, May 15, 2009, pp. 4134-4142.
Lotan, Is TIG1 a new tumor suppressor in prostate cancer, Journal of the National Cancer institute, vol. 94, No. 7, 2002, pp. 469-470.
Manna et al., Suppression of microtubule dynamic instability by the +TIP protein EB1 and its modulation by the CAP-Gly domain of p150glued, Biochemistry, vol. 47, No. 2, Jan. 15, 2008, pp. 779-786.
Mark et al., Function of retinoid nuclear receptors: lessons from genetic and pharmacological dissections of the retinoic acid signaling pathway during mouse embryogenesis, Annual Review of Pharmacology and Toxicology, vol. 46, 2006, pp. 451-480.
Mialhe et al., Tubulin detyrosination is a frequent occurrence in breast cancers of poor prognosis, Cancer Research, vol. 61, No. 13, Jul. 1, 2001, pp. 5024-5027.
Mitchell et al., Circulating microRNAs as stable blood-based markers for cancer detection, Proceedings of the National Academy of Sciences, U.S.A, vol. 105, No. 30, 2008, pp. 10513-10518.
Mizuiri et al., DNA methylation of genes linked to retinoid signaling in squamous cell carcinoma of the esophagus: DNA methylation of CRBP1 and TIG1 is associated with tumor stage, Cancer Science, vol. 96, No. 9, Sep. 2005, pp. 571-577.
Mordan et al., Calcium, Vitamin D and the Vitamin D Receptor: Impact on Prostate and Breast Cancer in Preclinical Models, Nutrition Reviews, vol. 65, Aug. 2007, pp. S131-S133.
Mucci et al., Vitamin D and prostate cancer risk—a less sunny outlook?, Journal of the National Cancer Institute, vol. 100, 2008, pp. 759-761.
Nagpal et al., Tazarotene-induced gene 1 (TIG1), a novel retinoic acid receptor-responsive gene in skin, Journal of Investigative Dermatology, vol. 106, No. 2, Feb. 1996, pp. 269-274.
Neuhouser et al., Dietary supplement use and prostate cancer risk in the Carotene and Retinol Efficacy Trial, Cancer Epidemiol.Biomarkers Prev, vol. 18, No. 8, Aug. 2009, pp. 2202-2206.
Normant et al., Carboxypeptidase A isoforms produced by distinct genes or alternative splicing in brain and other extrapancreatic tissues, The Journal of Biological Chemistry, vol. 270, No. 35, Sep. 1, 1995, pp. 20543-20549.
Normant et al., Purification, cDNA cloning, functional expression, and characterization of a 26-kDa endogenous mammalian carboxypeptidase inhibitor, Proceedings of the National Academy of Sciences, U.S.A, vol. 92, No. 26, Dec. 1995, pp. 12225-12229.
Orford et al., Serine phosphorylation-regulated ubiquitination and degradation of beta-catenin, The Journal of Biological Chemistry, vol. 272, No. 40, Oct. 3, 1997, pp. 24735-24738.
International Application No. PCT/US2012/025069, International Preliminary Report on Patentability mailed on Aug. 29, 2013, 11 pages.
International Application No. PCT/US2012/025069, International Search Report & Written Opinion mailed on Jul. 9, 2012, 16 pages.
Perkins et al., Association of antioxidants with memory in a multiethnic elderly sample using the Third National Health and Nutrition Examination Survey, American Journal of Epidemiology, vol. 150, No. 1, Jul. 1, 1999, pp. 37-44.
Pu et al., Differential expression of C-CAM cell adhesion molecule in prostate carcinogenesis in a transgenic mouse model, Journal of Urology, vol. 162, Sep. 1999, pp. 892-896.
Rodriguez et al., Nna1-like proteins are active metallocarboxypeptidases of a new and diverse M14 subfamily, FASEB Journal, vol. 21, No. 3, Mar. 2007, pp. 851-865.

Rupp et al., Xenopus embryos regulate the nuclear localization of XMyo, Genes & Development, vol. 8, No. 11, Jun. 1, 1994, pp. 1311-1323.
Sahab et al., Alteration in protein expression in estrogen receptor alpha-negative human breast cancer tissues indicates a malignant and metastatic phenotype, Clinical and Experimental Metastasis, vol. 27, No. 7, 2010, pp. 493-503.
Sahab et al., Anion exchange fractionation of serum proteins versus albumin elimination, Analytical Biochemistry, vol. 368, No. 1, Sep. 1, 2007, pp. 24-32.
Sahab et al., Isoelectric point-based prefractionation of proteins from crude biological samples prior to two-dimensional dimensional gel electrophoresis, Journal of Proteome Research, vol. 4, No. 6, 2005, pp. 2266-2272.
Sahab et al., Methodology and Applications of Disease Biomarker Identification in Human Serum, Biomarker Insights, vol. 2, Feb. 14, 2007, pp. 21-43.
Sahab et al., Tumor suppressor RARRES1 interacts with cytoplasmic carboxypeptidase AGBL2 to regulate the $\alpha$-tubulin tyrosination cycle, Cancer Research, vol. 71, No. 4, Feb. 15, 2011, pp. 1219-1228.
Sahab et al.,Tumor Suppressor RARRES1 Regulates DLG2, PP2A, VCP, EB1, and Ankrd26, Journal of cancer, vol. 1, Jun. 2, 2010, pp. 14-22.
Schwartz, Vitamin D and intervention trials in prostate cancer: from theory to therapy, Annals of Epidemiology, vol. 19, 2009, pp. 96-102.
Scragg et al., Serum 25-hydroxyvitamin D, ethnicity, and blood pressure in the Third National Health and Nutrition Examination Survey, American Journal of Hypertension, vol. 20, No. 7, Jul. 2007, pp. 713-719.
Shah et al.,The molecular basis of vitamin D receptor and beta-catenin crossregulation, Molecular Cell, vol. 21, No. 6, Mar. 17, 2006, pp. 799-809.
Shappell et al., Prostate pathology of genetically engineered mice: definitions and classification. The consensus report from the Bar Harbor meeting of the Mouse Models of Human Cancer Consortium Prostate Pathology Committee, Cancer Research, vol. 64, No. 6, Mar. 15, 2004, pp. 2270-2305.
Shi et al., Chromosome nondisjunction yields tetraploid rather than aneuploid cells in human cell lines, Nature, vol. 437, No. 7061, Oct. 13, 2005, pp. 1038-1042.
Shutoh et al., DNA methylation of genes linked with retinoid signaling in gastric carcinoma: expression of the retinoid acid receptor beta, cellular retinol-binding protein 1, and tazarotene-induced gene 1 genes is associated with DNA methylation, Cancer, vol. 104, No. 8, Oct. 15, 2005, pp. 1609-1619.
So et al., Multiple tumor suppressor genes are increasingly methylated with age in non-neoplastic gastric epithelia, Cancer Science, vol. 97, No. 11, Nov. 2006, pp. 1155-1158.
Stevens et al., Use of multivitamins and prostate cancer mortality in a large cohort of US men, Cancer Causes Control, vol. 16, No. 6, Aug. 2005, pp. 643-650.
Sung et al., Tumor suppressor function of Syk in human MCF10A in vitro and normal mouse mammary epithelium in vivo, PLoS ONE, vol. 4, No. 10, Oct. 15, 2009, e7445.
Takai et al., Discovery of epigenetically masked tumor suppressor genes in endometrial cancer, Molecular Cancer Research, vol. 3, No. 5, May 3, 2005, pp. 261-269.
Takiguchi-Hayashi et al., Latexin expression in smaller diameter primary sensory neurons in the rat, Brain Research, vol. 801, Aug. 10, 1998, pp. 9-20.
Tokumaru et al., Is TIG1 a new tumor suppressor in prostate cancer?, 2003, pp. 919-920.
Uratani et al., Latexin, a carboxypeptidase a inhibitor, is expressed in rat peritoneal mast cells and is associated with granular structures distinct from secretory granules and lysosomes, Biochemical Journal, vol. 346, Mar. 15, 2000, pp. 817-826.
Vieth, How to optimize vitamin D supplementation to prevent cancer, based on cellular adaptation and hydroxylase enzymology, Anticancer Research, vol. 29, No. 9, Sep. 2009, pp. 3675-3684.
Wang et al., The carboxypeptidase-like substrate-binding site in Nna1 is essential for the rescue of the Purkinje cell degeneration (pcd) phenotype, Molecular and Cellular Neuroscience, vol. 33, No. 2, Oct. 2006, pp. 200-213.

(56) References Cited

OTHER PUBLICATIONS

Westermann et al., Post-translational modifications regulate microtubule function, Nature Reviews Molecular Cell Biology, vol. 4, Dec. 2003, pp. 938-948.

Whipple et al., Epithelial-to-mesenchymal transition promotes tubulin detyrosination and microtentacles that enhance endothelial engagement, Cancer Research, vol. 70, No. 20, Oct. 15, 2010, pp. 8127-8137.

Wood et al., DNA microarray analysis of vitamin D-induced gene expression in a human colon carcinoma cell line, Physiol Genomics, vol. 17, Jan. 1, 2004, pp. 122-129.

Wu et al., Integrin-linked Protein Kinase Regulates Fibronectin Matrix Assembly, E-cadherin Expression, and Tumorigenicity, The Journal of Biological Chemistry, vol. 273, Jan. 2, 1998, pp. 528-538.

Youssef et al., Hypermethylation and silencing of the putative tumor suppressor Tazarotene-induced gene 1 in human cancers, Cancer Research, vol. 64, No. 7, Apr. 2004, pp. 2411-2417.

Zhang et al., Methylation of the retinoid response gene TIG1 in prostate cancer correlates with methylation of the retinoic acid receptor beta gene, Oncogene, vol. 23, Mar. 18, 2004, pp. 2241-2249.

Argarana et al., Release of [C-14]Tyrosine from Tubulinyl-[C-14]Tyrosine by Brain Extract—Separation of a Carboxypeptidase from Tubulin-Tyrosine Ligase, Molecular & Cellular Biology, vol. 19, No. 1, 1978, pp. 17-21.

Barra et al., Posttranslational tyrosination/detyrosination of tubulin, Molecular Neurobiology, vol. 2, No. 2, 1988, pp. 133-153.

Chen et al., Enzyme-catalysed Selective Ester Hydrolysis of Aspartyl and Glutamyl Dipeptide Benzyl Esters, Journal of Chemical Research, Synopses, vol. 9, 1987, pp. 308-309.

Grant et al., Possible role of serum 25-hydroxyvitamin D in black-white health disparities in the United States, Journal of the American Medical Directors Association, vol. 11, 2010, pp. 617-628.

Guyton et al., Vitamin D and vitamin D analogs as cancer chemopreventive agents, Nutrition Reviews, vol. 61, 2003, pp. 227-238.

Hanks, Signaling through focal adhesion kinase, Bioessays, vol. 19, No. 2, 1997, pp. 137-145.

Hatanaka et al., Intracortical regionality represented by specific transcription for a novel protein, European Journal of Neuroscience, vol. 6, No. 6, 1994, pp. 973-982.

Kwong et al., Silencing of the retinoid response gene TIG1 by promoter hypermethylation in nasopharyngeal carcinoma, Int. J. Cancer, vol. 113, 2005, pp. 386-392.

Njar et al., Retinoic acid metabolism blocking agents (RAMBAs) for treatment of cancer and dermatological diseases, Bioorganic & Medicinal Chemistry, vol. 14, No. 13, Jul. 1, 2006, pp. 4323-4340.

Ohnishi et al., Involvement of tazarotene-induced gene 1 in proliferation and differentiation of human adipose tissue-derived mesenchymal stem cells, Cell Proliferation, vol. 42, No. 3, Jun. 2009, pp. 309-316.

Rambow et al., Identification of differentially expressed genes in spontaneously regressing melanoma using the MeLiM Swine Model, Pigment Cell Melanoma Research, vol. 21, No. 2, Apr. 2008, pp. 147-161.

Schenk et al., Serum Retinol and Prostate Cancer Risk: a Nested Case-Control Study in the Prostate, Lung, Colorectal, and Ovarian Cancer Screening Trial, Cancer Epidemiol. Biomarkers Prev., vol. 18, 2009, pp. 1227-1237.

Soucek et al., Normal and prostate cancer cells display distinct molecular profiles of alpha-tubulin posttranslational modifications, Prostate, vol. 66, No. 9, Jun. 15, 2006, pp. 954-965.

Takiguchi-Hayashi, Restricted expression of latexin in dorsal midline cells of developing rat forebrain, Neuroreport, vol. 6, No. 2, Jan. 26, 1995, pp. 281-283.

* cited by examiner

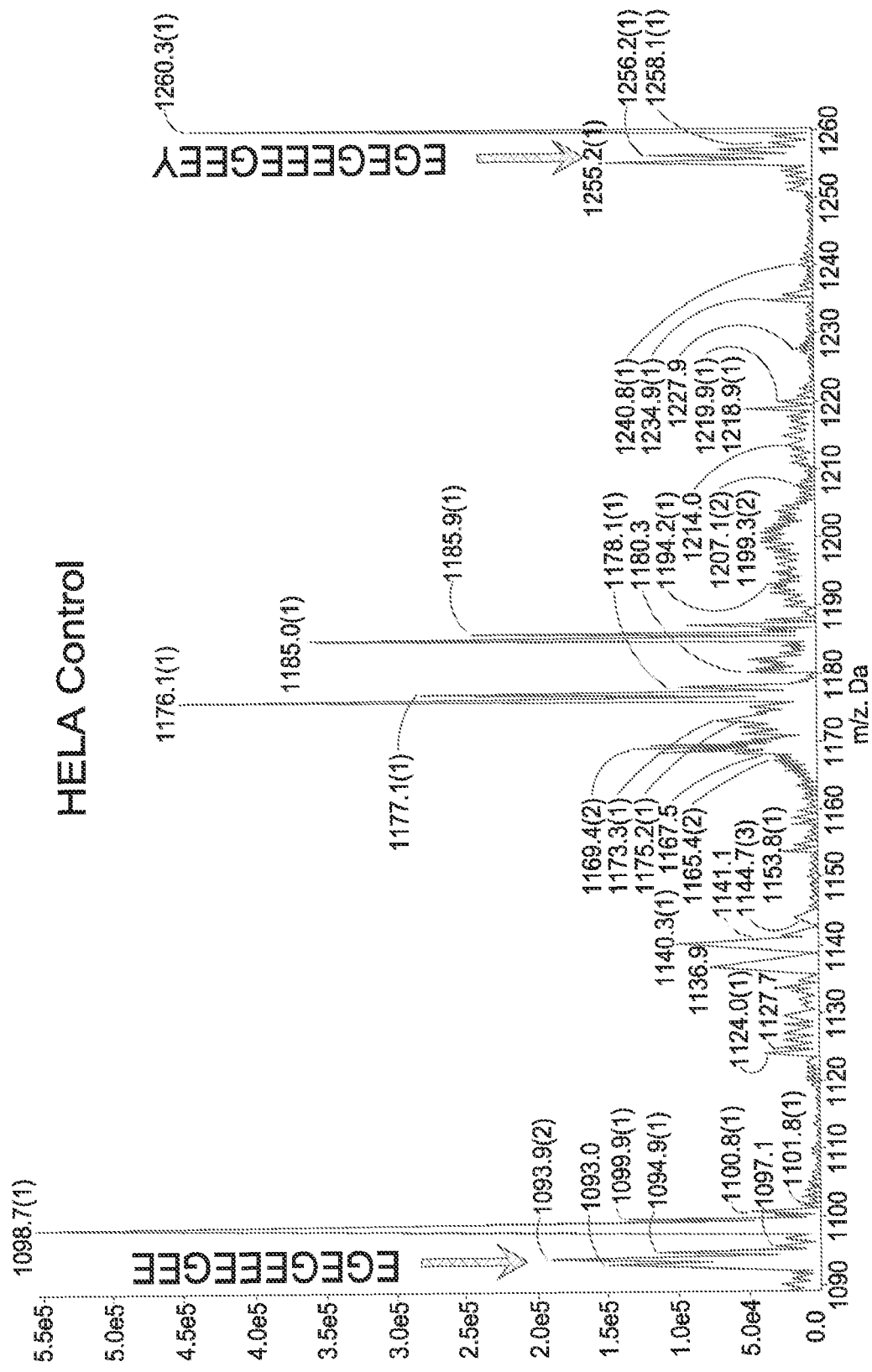

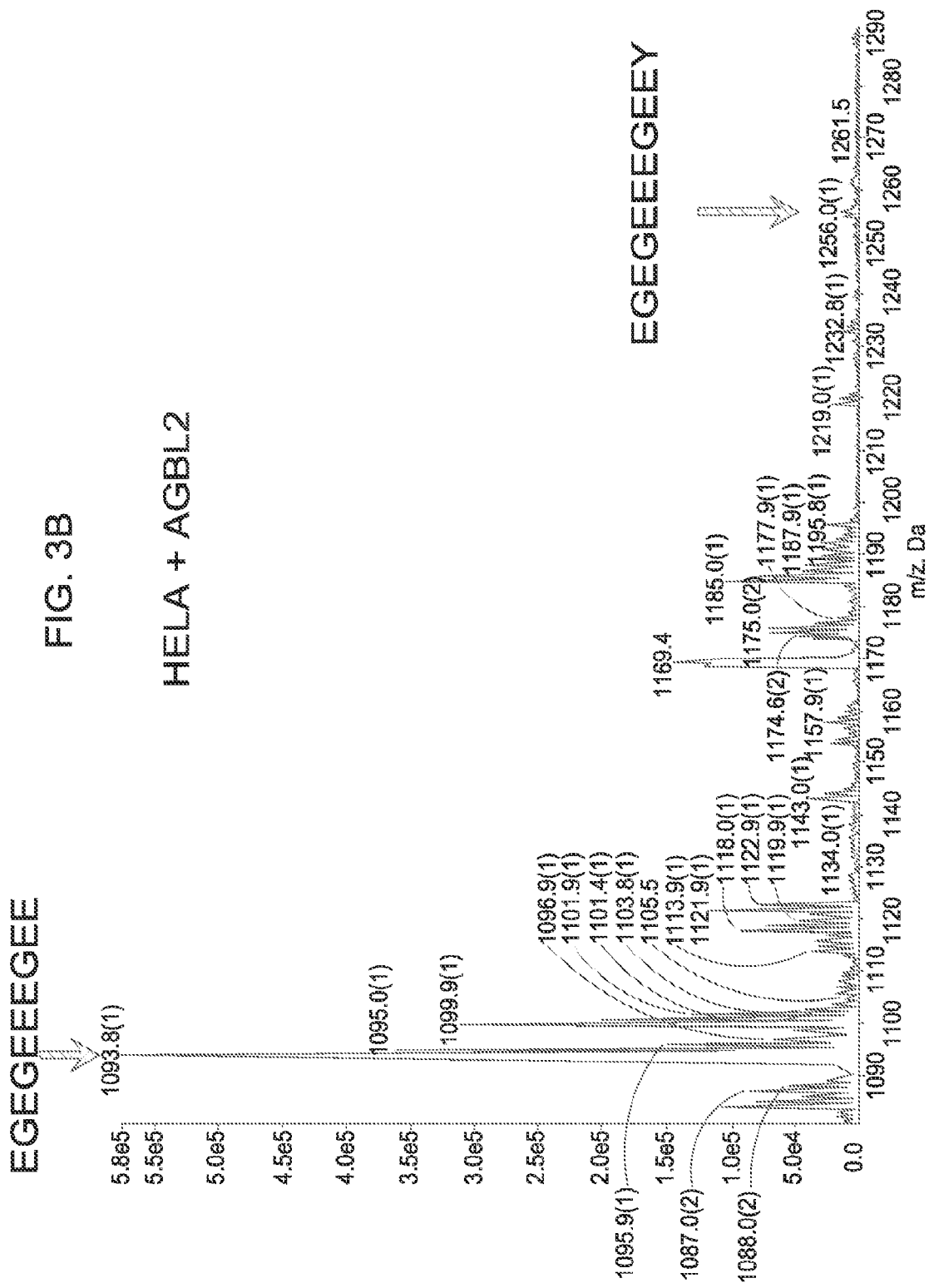

SMALL MOLECULE INHIBITORS OF AGBL2

CROSS-REFERENCE TO PRIORITY APPLICATION

This application claims priority to U.S. Provisional Application No. 61/443,069, filed Feb. 15, 2011, which is incorporated herein by reference in its entirety.

BACKGROUND

The removal of the C-terminal tyrosine of α-tubulin to form detyrosinated α-tubulin is involved in several aspects of microtubule function, including kinesin interactions, spindle dynamics, mitosis, and neuronal specification. Microtubules containing large amounts of detyrosinated α-tubulin are more stable and resistant to depolymerization by destabilizing agents. Further, detyrosinated α-tubulin has been shown to be elevated in aggressive breast and prostate cancers.

SUMMARY

Provided herein are small molecule inhibitors of ATP/GTP binding protein like 2 (AGBL2) and their use in methods for treating or preventing cancer and neurologic disorders. A class of compounds described herein includes compounds of the following structure:

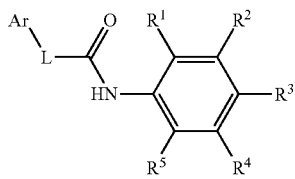

and pharmaceutically acceptable salts or prodrugs thereof. In these compounds, Ar is substituted or unsubstituted aryl or substituted or unsubstituted heteroaryl; L is absent or —(CHR$^6$)—, wherein R$^6$ is substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl; and R$^1$, R$^2$, R$^3$, R$^4$, and R$^5$ are each independently selected from hydrogen, halogen, hydroxyl, cyano, nitro, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl. Optionally, if L is absent and Ar is

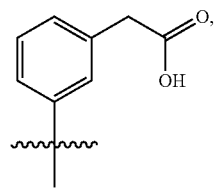

then R$^2$ and R$^3$ are not combined to form 1,3-dioxolane.

A class of compounds described herein includes compounds of the following structure:

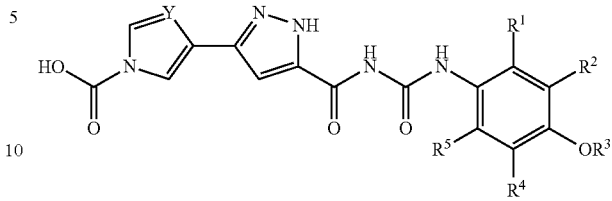

and pharmaceutically acceptable salts or prodrugs thereof. In these compounds, R$^1$, R$^2$, R$^4$, and R$^5$ are each independently selected from hydrogen, halogen, hydroxyl, cyano, nitro, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl; R$^3$ is hydrogen, substituted or unsubstituted alkyl, or substituted or unsubstituted carbonyl; and Y is CH or N.

A class of compounds described herein includes compounds of the following structure:

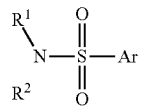

and pharmaceutically acceptable salts or prodrugs thereof. In these compounds, R$^1$ and R$^2$ are each independently selected from hydrogen, substituted or unsubstituted alkyl, substituted or unsubstituted cycloalkyl, substituted or unsubstituted aryl, or substituted or unsubstituted heteroaryl; and Ar is substituted or unsubstituted aryl or substituted or unsubstituted heteroaryl. A class of compounds described herein includes compounds of the following structure:

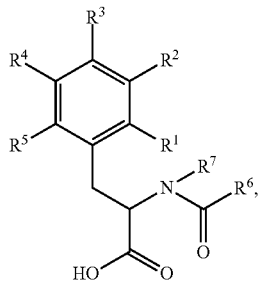

and pharmaceutically acceptable salts or prodrugs thereof. In these compounds, R$^1$, R$^2$, R$^3$, R$^4$, and R$^5$ are each independently selected from hydrogen, halogen, hydroxyl, trifluoromethyl, cyano, nitro, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl; R$^6$ is substituted or unsubstituted alkyl, substituted or unsubstituted heteroalkyl, substituted or unsubstituted amino, substituted or unsubstituted aryl, substituted or unsubstituted heteroaryl, substituted or unsubstituted carbonyl, or substituted or unsubstituted carboxyl; and $R^7$ is hydrogen or substituted or unsubstituted alkyl.

A class of compounds described herein includes compounds of the following structure:

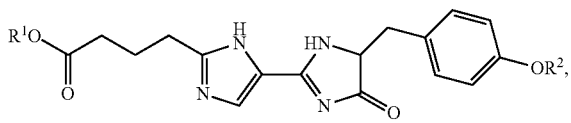

and pharmaceutically acceptable salts or prodrugs thereof. In these compounds, $R^1$ is hydrogen or substituted or unsubstituted alkyl; and $R^2$ is hydrogen, substituted or unsubstituted alkyl, or substituted or unsubstituted carbonyl.

Also provided herein are compositions including a compound as described above and a pharmaceutically acceptable carrier.

Further provided herein are methods of preventing or treating cancer or a neurologic disorder in a subject. A method for treating or preventing cancer or a neurologic disorder in a subject includes administering to the subject an effective amount of a compound of the following formula:

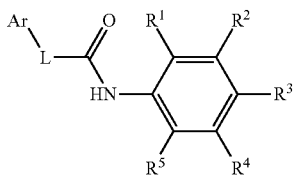

or a pharmaceutically acceptable salt or prodrug thereof, or a composition comprising the compound and a pharmaceutically acceptable carrier. In this method, Ar is substituted or unsubstituted aryl or substituted or unsubstituted heteroaryl; L is absent or —(CHR$^6$)—, wherein $R^6$ is substituted or unsubstituted alkyl, substituted or unsubstituted alkenyl, substituted or unsubstituted alkynyl, substituted or unsubstituted cycloalkyl, substituted or unsubstituted heterocycloalkyl, substituted or unsubstituted aryl, or substituted or unsubstituted heteroaryl; and $R^1$, $R^2$, $R^3$, $R^4$, and $R^5$ are each independently selected from hydrogen, halogen, hydroxyl, cyano, nitro, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl. Optionally, $R^2$ and $R^3$ combine to form a substituted or unsubstituted heterocycloalkyl. Optionally, Ar is selected from the group consisting of:

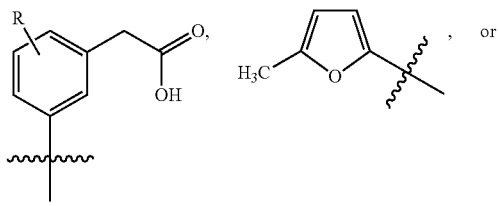

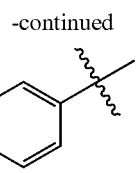

wherein R is trifluoromethyl, chloro, fluoro, methoxy, amino, or nitro.

A method of treating or preventing cancer or a neurologic disorder in a subject includes administering to the subject an effective amount of one or more compounds of the following structure:

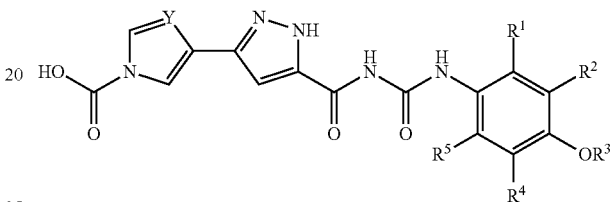

or a pharmaceutically acceptable salt or prodrug thereof, or a composition comprising the compound and a pharmaceutically acceptable carrier. In this method, $R^1$, $R^2$, $R^4$, and $R^5$ are each independently selected from hydrogen, halogen, hydroxyl, cyano, nitro, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl; $R^3$ is hydrogen, substituted or unsubstituted alkyl, or substituted or unsubstituted carbonyl; and Y is CH or N.

A method of treating or preventing cancer or a neurologic disorder in a subject includes administering to the subject an effective amount of one or more compounds of the following structure:

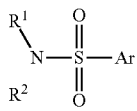

or a pharmaceutically acceptable salt or prodrug thereof, or a composition comprising the compound and a pharmaceutically acceptable carrier. In this method, $R^1$ and $R^2$ are each independently selected from hydrogen, substituted or unsubstituted alkyl, substituted or unsubstituted cycloalkyl, substituted or unsubstituted aryl, or substituted or unsubstituted heteroaryl; and Ar is substituted or unsubstituted aryl or substituted or unsubstituted heteroaryl. Optionally, $R^1$ and $R^2$ combine to form a substituted or unsubstituted cycloalkyl. Optionally, Ar is selected from the group consisting of:

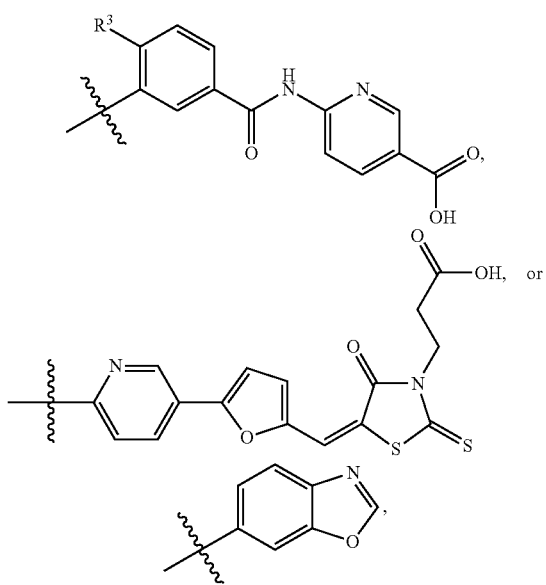

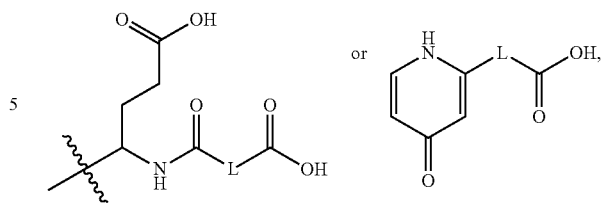

wherein L is selected from substituted or unsubstituted alkyl, substituted or unsubstituted aryl, or substituted or unsubstituted heteroaryl.

A method of treating or preventing cancer or a neurologic disorder in a subject includes administering to the subject an effective amount of one or more compounds of the following structure:

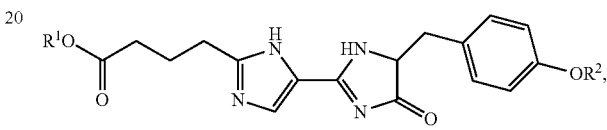

or a pharmaceutically acceptable salt or prodrug thereof, or a composition comprising the compound and a pharmaceutically acceptable carrier. In this method, $R^1$ is hydrogen or substituted or unsubstituted alkyl; and $R^2$ is hydrogen, substituted or unsubstituted alkyl, or substituted or unsubstituted carbonyl, or a pharmaceutically acceptable salt or prodrug thereof, or a composition comprising the compound and a pharmaceutically acceptable carrier.

A method of treating or preventing cancer or a neurologic disorder in a subject includes administering to the subject an effective amount of one or more compounds of the following structure:

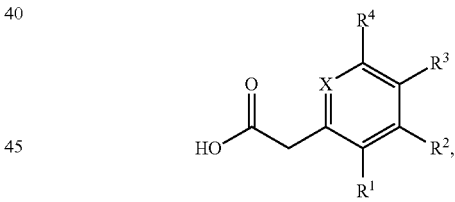

or a pharmaceutically acceptable salt or prodrug thereof, or a composition comprising the compound and a pharmaceutically acceptable carrier. In this method, $R^1$ is methyl or substituted thio; $R^2$, $R^3$, and $R^4$ are each independently selected from hydrogen, halogen, or trifluoromethyl; and X is N or CH.

Optionally, the methods of treating or preventing cancer in a subject further include administering a second therapeutic agent (e.g., a chemotherapeutic agent) to the subject. Further, the methods of treating or preventing a neurologic disorder in a subject optionally include administering a second therapeutic agent, such as an anti-depressant or an anxiolytic, to the subject.

Also provided herein are the compounds as described above.

The details of one or more embodiments are set forth in the drawings and the description below. Other features, objects, and advantages will be apparent from the description and drawings, and from the claims.

wherein $R^3$ is hydrogen or a halogen.

A method of treating or preventing cancer or a neurologic disorder in a subject includes administering to the subject an effective amount of one or more compounds of the following structure:

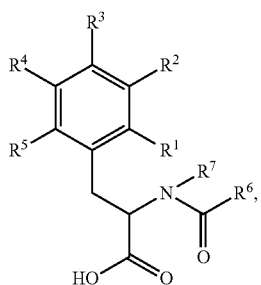

or a pharmaceutically acceptable salt or prodrug thereof, or a composition comprising the compound and a pharmaceutically acceptable carrier. In this method, $R^1$, $R^2$, $R^3$, $R^4$, and $R^5$ are each independently selected from hydrogen, halogen, hydroxyl, trifluoromethyl, cyano, nitro, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl; $R^6$ is substituted or unsubstituted alkyl, substituted or unsubstituted heteroalkyl, substituted or unsubstituted amino, substituted or unsubstituted aryl, substituted or unsubstituted heteroaryl, substituted or unsubstituted carbonyl, or substituted or unsubstituted carboxyl; and $R^7$ is hydrogen or substituted or unsubstituted alkyl. Optionally, $R^6$ is selected from the group consisting of

DESCRIPTION OF DRAWINGS

FIGS. 3A and 3B show mass spectra showing the detyrosinated (1093.3 Da) and tyrosinated (1256.4 Da) tubulin CTT in control (FIG. 3A) and AGBL2 treated lysates (FIG. 3B). The detyrosinated to tyrosinated ratio of tubulin increased from 1.20 to 41.4 following AGBL2 treatment.

DETAILED DESCRIPTION

Figure 1:
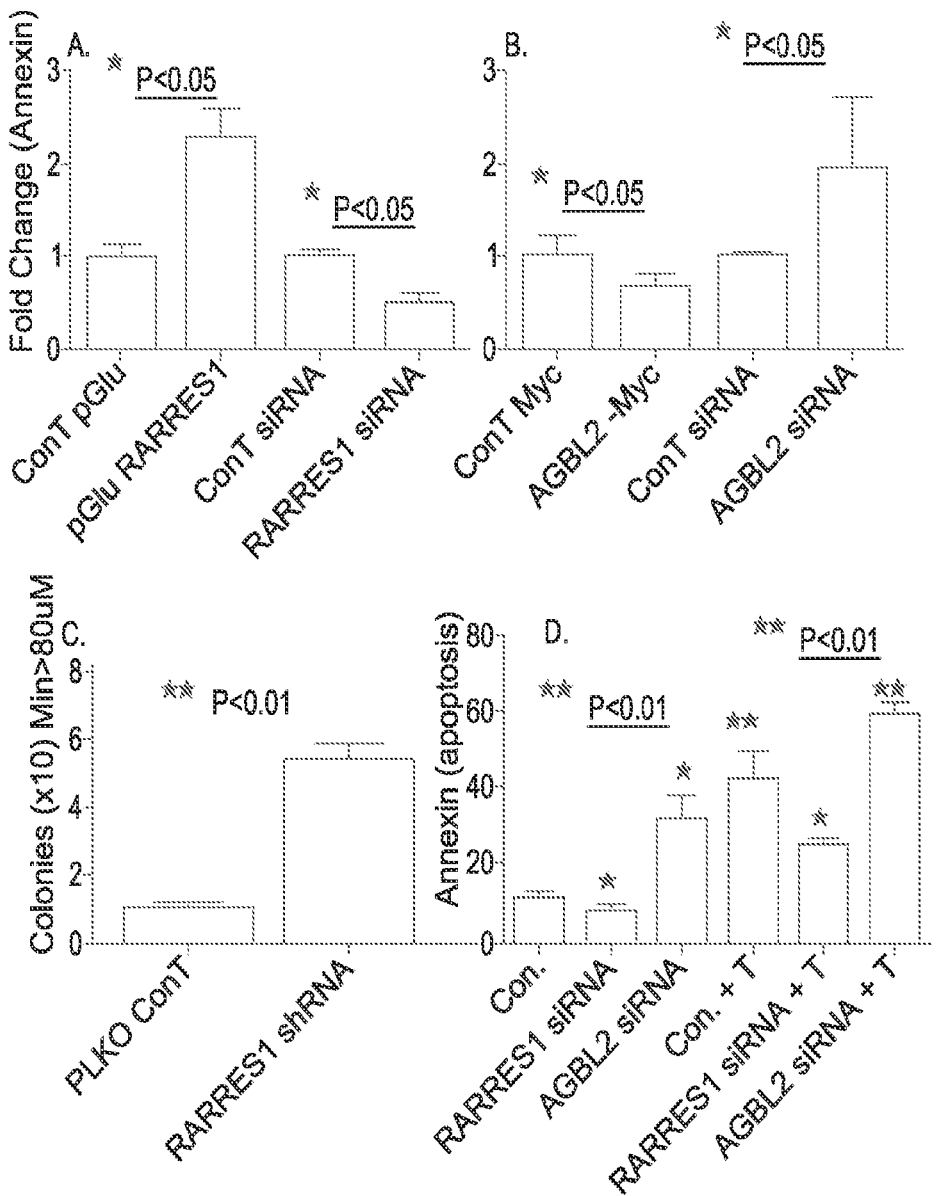
FIG. 1 contains graphs showing the exogenous expression (pGlu-RARRES1; AGBL2) and knock-down (si/sh) of RARRES1 and AGBL2 through annexin staining (Panels A and B), soft agar colony formation (Panel C), and taxol response (Panel D).

Described herein are compounds for use as ATP/GTP binding protein like 2 (AGBL2) inhibitors and methods for treating and preventing AGBL2 related disorders, including cancer and neurologic disorders, in a subject. The methods of preventing or treating cancer or a neurologic disorder described herein include administering to the subject an AGBL2 inhibitor. Such inhibitors are administered in an effective amount to prevent or treat one or more symptoms of cancer or neurologic disorders.

I. Compounds

A class of AGBL2 inhibitors useful in the methods described herein includes compounds represented by Formula I:

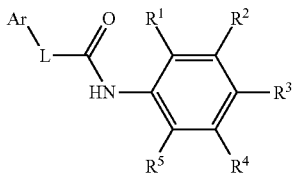

I or a pharmaceutically acceptable salt or prodrug thereof.

In Formula I, Ar is substituted or unsubstituted aryl or substituted or unsubstituted heteroaryl. Optionally, Ar is one of Structure I-A, Structure I-B, or Structure I-C:

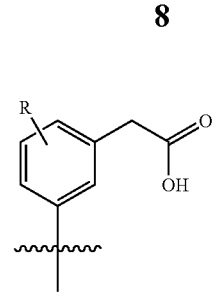

Structure I-A

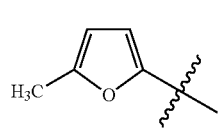

Structure I-B

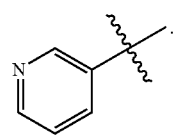

Structure I-C

In Structure I-A, R can be, for example, hydrogen, trifluoromethyl, chloro, fluoro, methoxy, amino, or nitro. The R group can be located at any position on the ring.

Also in Formula I, L is absent or —(CHR$^6$)—, wherein R$^6$ is substituted or unsubstituted alkyl (e.g., C$_{1-4}$alkyl), substituted or unsubstituted alkenyl (e.g., C$_{2-4}$ alkenyl), substituted or unsubstituted alkynyl (e.g., C$_{2-4}$alkynyl), substituted or unsubstituted cycloalkyl, substituted or unsubstituted heterocycloalkyl, substituted or unsubstituted aryl, or substituted or unsubstituted heteroaryl.

Additionally in Formula I, R$^1$, R$^2$, R$^3$, R$^4$, and R$^5$ are each independently selected from hydrogen, halogen, hydroxyl, cyano, nitro, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl.

In Formula I, R$^2$ and R$^3$ are optionally combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl.

Examples of Formula I include the following compounds:

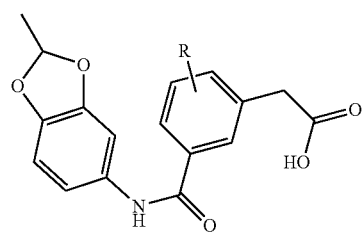

Sd-4-1

-continued

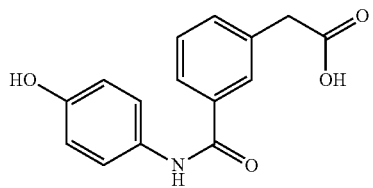
Sd-4-2

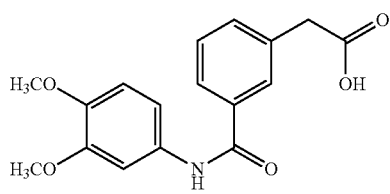
Sd-4-3

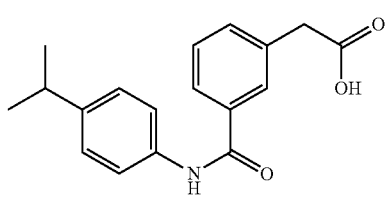
Sd-4-4

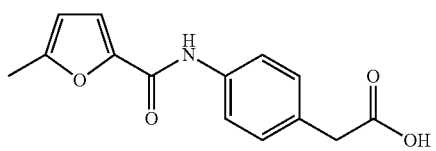
Sd-4-5

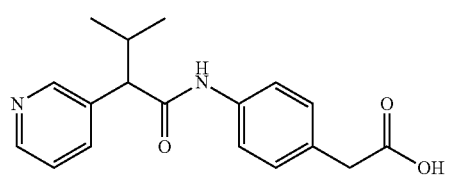
Sd-4-6

In Compound Sd-4-1, R can be, for example, hydrogen, trifluoromethyl, halogen (e.g., chloro or fluoro), alkoxy (e.g., methoxy), amino, or nitro. The R group can be located at any position on the ring.

In some examples of Formula I, the compound is not Sd-4-5.

In some examples of Formula I, if L is absent and Ar is Structure I-A, wherein R is hydrogen, then $R^2$ and $R^3$ are not combined to form 1,3-dioxolane. In other words, in some examples, the compound of Formula I is not

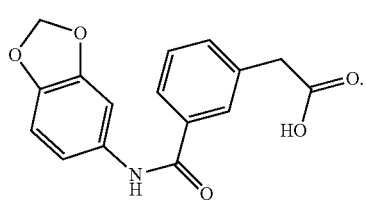
Sd-4

A class of AGBL2 inhibitors useful in the methods described herein includes compounds represented by Formula II:

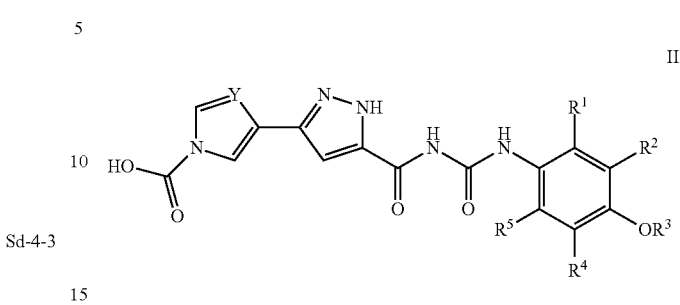
II or a pharmaceutically acceptable salt or prodrug thereof.

In Formula II, $R^1$, $R^2$, $R^4$, and $R^5$ are each independently selected from hydrogen, halogen, hydroxyl, cyano, nitro, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl.

Also in Formula II, $R^3$ is hydrogen, substituted or unsubstituted alkyl, or substituted or unsubstituted carbonyl.

Additionally in Formula II, Y is CH or N.

Examples of Formula II include the following compounds

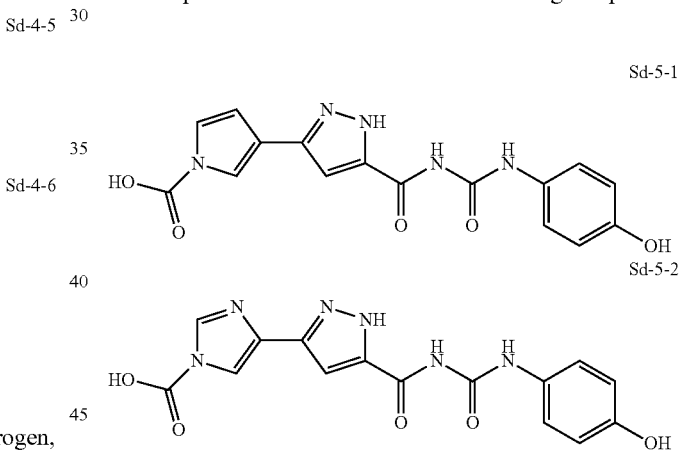

Sd-5-1

Sd-5-2

A class of AGBL2 inhibitors useful in the methods described herein includes compounds represented by Formula III:

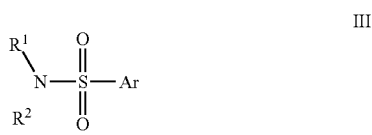
III or a pharmaceutically acceptable salt or prodrug thereof.

In Formula III, $R^1$ and $R^2$ are each independently selected from hydrogen, substituted or unsubstituted $C_1$-$C_6$ alkyl, substituted or unsubstituted cycloalkyl, substituted or unsubstituted aryl, or substituted or unsubstituted heteroaryl.

Also in Formula III, Ar is substituted or unsubstituted aryl or substituted or unsubstituted heteroaryl. Optionally, Ar is one of Structure III-A, Structure III-B, or Structure III-C Structure III-A

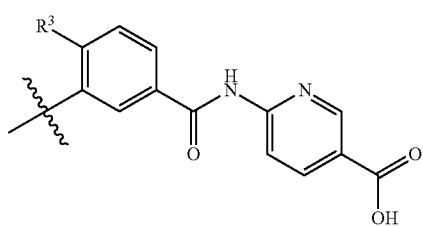

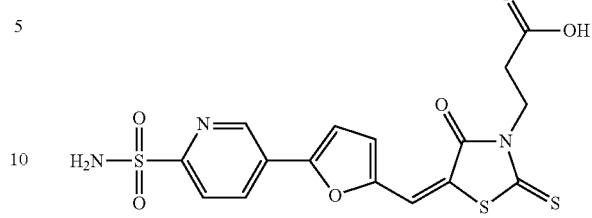

Sd-5-5

Structure III-B

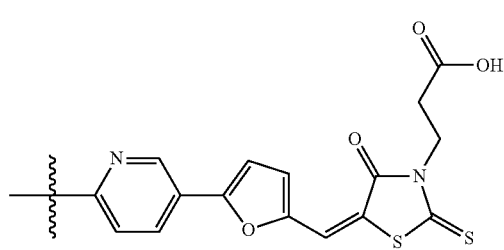

In some examples of Formula III, the compound is not Sd-5-5.

A class of AGBL2 inhibitors useful in the methods described herein includes compounds represented by Formula IV:

Structure III-C

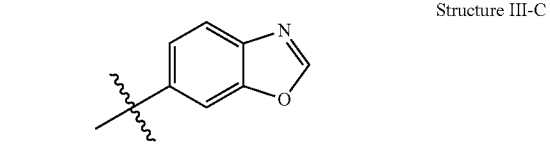

IV

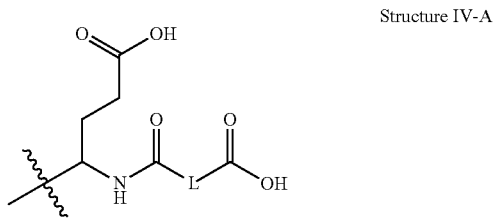

In Structure III-A, $R^3$ can be, for example, hydrogen or halogen (e.g., Cl, F, or Br).

In Formula III, $R^1$ and $R^2$ are optionally combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl.

Examples of Formula III include the following compounds:

or a pharmaceutically acceptable salt or prodrug thereof.

In Formula IV, $R^1$, $R^2$, $R^3$, $R^4$, and $R^5$ are each independently selected from hydrogen, halogen, hydroxyl, trifluoromethyl, cyano, nitro, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl.

Also in Formula IV, $R^6$ is substituted or unsubstituted alkyl, substituted or unsubstituted heteroalkyl, substituted or unsubstituted amino, substituted or unsubstituted aryl, substituted or unsubstituted heteroaryl, substituted or unsubstituted carbonyl, or substituted or unsubstituted carboxyl. Optionally, $R^6$ is one of Structure IV-A or Structure IV-B:

Sd-5-3

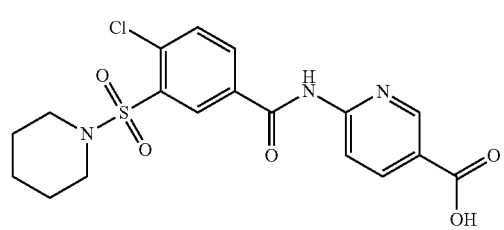

Sd-5-4

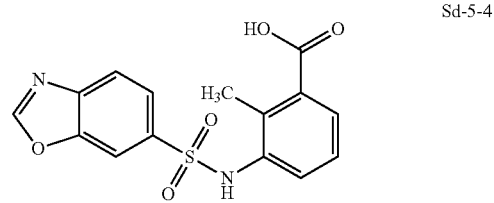

Structure IV-A

-continued

Structure IV-B

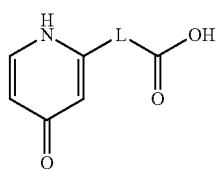

In Structures IV-A and IV-B, L is selected from substituted or unsubstituted alkyl, substituted or unsubstituted aryl, or substituted or unsubstituted heteroaryl.

Additionally, in Formula IV, $R^7$ is hydrogen or substituted or unsubstituted alkyl.

Examples of Formula IV include the following compounds:

Sd-6-1

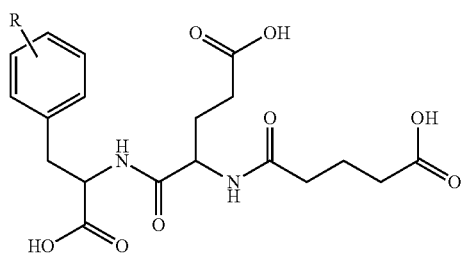

Sd-6-2

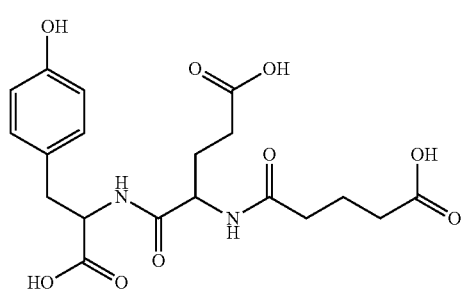

Sd-6-3

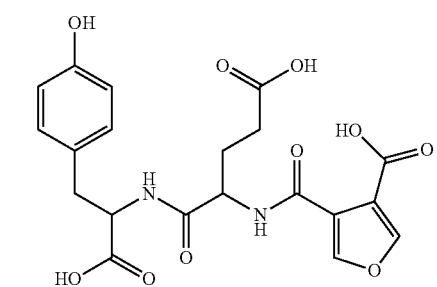

Sd-6-4

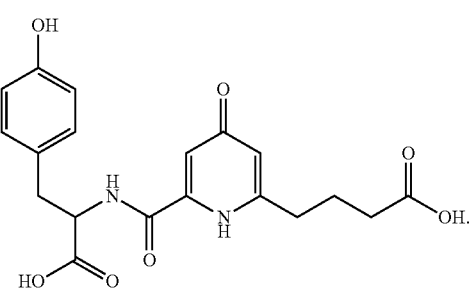

In Compound Sd-6-1, R can be, for example, trifluoromethyl or halogen (e.g., chloro or fluoro). The R group can be located at any position on the ring.

A class of AGBL2 inhibitors useful in the methods described herein includes compounds represented by Formula V:

V

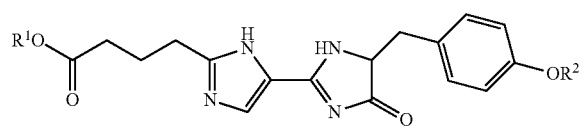

or a pharmaceutically acceptable salt or prodrug thereof.

In Formula V, $R^1$ is hydrogen or substituted or unsubstituted alkyl.

Also in Formula V, $R^2$ is hydrogen, substituted or unsubstituted alkyl, or substituted or unsubstituted carbonyl.

A particular example of Formula V includes the following compound:

Sd-6-5

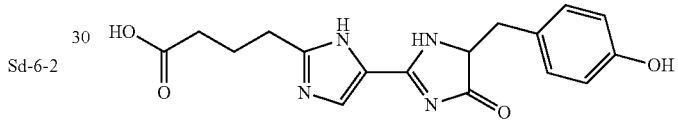

A class of AGBL2 inhibitors useful in the methods described herein includes compounds represented by Formula VI:

VI

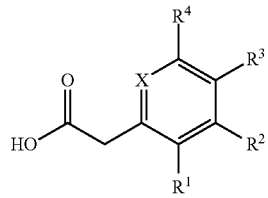

or a pharmaceutically acceptable salt or prodrug thereof.

In Formula VI, $R^1$ is methyl or substituted thio.

Also in Formula VI, $R^2$, $R^3$, and $R^4$ are each independently selected from hydrogen, halogen, or trifluoromethyl.

Additionally in Formula VI, X is N or CH.

Examples of Formula VI include the following compounds:

Sd-1

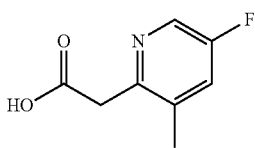

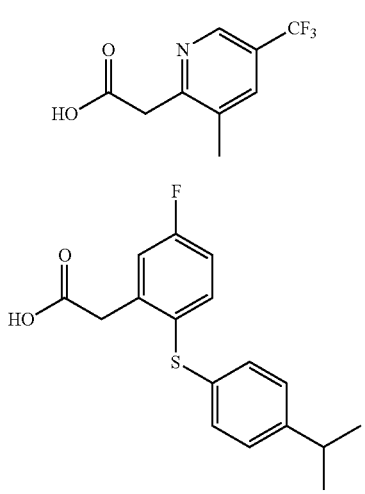

As used herein, the terms alkyl, alkenyl, and alkynyl include straight- and branched-chain monovalent substituents. Examples include methyl, ethyl, isobutyl, 3-butynyl, and the like. Ranges of these groups useful with the compounds and methods described herein include $C_1$-$C_{20}$ alkyl, $C_2$-$C_{20}$ alkenyl, and $C_2$-$C_{20}$ alkynyl. Additional ranges of these groups useful with the compounds and methods described herein include $C_1$-$C_{12}$ alkyl, $C_2$-$C_{12}$ alkenyl, $C_2$-$C_{12}$ alkynyl, $C_1$-$C_6$ alkyl, $C_2$-$C_6$ alkenyl, $C_2$-$C_6$ alkynyl, $C_1$-$C_4$ alkyl, $C_2$-$C_4$ alkenyl, and $C_2$-$C_4$ alkynyl.

Heteroalkyl, heteroalkenyl, and heteroalkynyl are defined similarly as alkyl, alkenyl, and alkynyl, but can contain O, S, or N heteroatoms or combinations thereof within the backbone. Ranges of these groups useful with the compounds and methods described herein include $C_1$-$C_{20}$ heteroalkyl, $C_2$-$C_{20}$ heteroalkenyl, and $C_2$-$C_{20}$ heteroalkynyl. Additional ranges of these groups useful with the compounds and methods described herein include $C_1$-$C_{12}$ heteroalkyl, $C_2$-$C_{12}$ heteroalkenyl, $C_2$-$C_{12}$ heteroalkynyl, $C_1$-$C_6$ heteroalkyl, $C_2$-$C_6$ heteroalkenyl, $C_2$-$C_6$ heteroalkynyl, $C_1$-$C_4$ heteroalkyl, $C_2$-$C_4$ heteroalkenyl, and $C_2$-$C_4$ heteroalkynyl.

The terms cycloalkyl, cycloalkenyl, and cycloalkynyl include cyclic alkyl groups having a single cyclic ring or multiple condensed rings. Examples include cyclohexyl, cyclopentylethyl, and adamantanyl. Ranges of these groups useful with the compounds and methods described herein include $C_3$-$C_{20}$ cycloalkyl, $C_3$-$C_{20}$ cycloalkenyl, and $C_3$-$C_{20}$ cycloalkynyl. Additional ranges of these groups useful with the compounds and methods described herein include $C_5$-$C_{12}$ cycloalkyl, $C_5$-$C_{12}$ cycloalkenyl, $C_5$-$C_{12}$ cycloalkynyl, $C_5$-$C_6$ cycloalkyl, $C_5$-$C_6$ cycloalkenyl, and $C_5$-$C_6$ cycloalkynyl.

The terms heterocycloalkyl, heterocycloalkenyl, and heterocycloalkynyl are defined similarly as cycloalkyl, cycloalkenyl, and cycloalkynyl, but can contain O, S, or N heteroatoms or combinations thereof within the cyclic backbone. Ranges of these groups useful with the compounds and methods described herein include $C_3$-$C_{10}$ heterocycloalkyl, $C_3$-$C_{20}$ heterocycloalkenyl, and $C_3$-$C_{20}$ heterocycloalkynyl. Additional ranges of these groups useful with the compounds and methods described herein include $C_5$-$C_{12}$ heterocycloalkyl, $C_5$-$C_{12}$ heterocycloalkenyl, $C_5$-$C_{12}$ heterocycloalkynyl, $C_5$-$C_6$ heterocycloalkyl, $C_5$-$C_6$ heterocycloalkenyl, and $C_5$-$C_6$ heterocycloalkynyl.

Aryl molecules include, for example, cyclic hydrocarbons that incorporate one or more planar sets of, typically, six carbon atoms that are connected by delocalized electrons numbering the same as if they consisted of alternating single and double covalent bonds. An example of an aryl molecule is benzene. Heteroaryl molecules include substitutions along their main cyclic chain of atoms such as O, N, or S. When heteroatoms are introduced, a set of five atoms, e.g., four carbon and a heteroatom, can create an aromatic system. Examples of heteroaryl molecules include furan, pyrrole, thiophene, imadazole, oxazole, pyridine, and pyrazine. Aryl and heteroaryl molecules can also include additional fused rings, for example, benzofuran, indole, benzothiophene, naphthalene, anthracene, and quinoline.

The alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl molecules used herein can be substituted or unsubstituted. As used herein, the term substituted includes the addition of an alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl group to a position attached to the main chain of the alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl, e.g., the replacement of a hydrogen by one of these molecules. Examples of substitution groups include, but are not limited to, hydroxyl, halogen (e.g., F, Br, Cl, or I), and carboxyl groups. Conversely, as used herein, the term unsubstituted indicates the alkyl, alkenyl, alkynyl, aryl, heteroalkyl, heteroalkenyl, heteroalkynyl, heteroaryl, cycloalkyl, cycloalkenyl, cycloalkynyl, heterocycloalkyl, heterocycloalkenyl, or heterocycloalkynyl has a full complement of hydrogens, i.e., commensurate with its saturation level, with no substitutions, e.g., linear decane (—$(CH_2)_9$—$CH_3$).

II. Pharmaceutical Formulations

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, may include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia Pa., 2005. Examples of physiologically acceptable carriers include buffers, such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers, such as polyvinylpyrrolidone; amino acids such as glycine, glutamine, asparagine, arginine or lysine; monosaccharides, disaccharides, and other carbohydrates, including glucose, mannose, or dextrins; chelating agents, such as EDTA; sugar alcohols, such as mannitol or sorbitol; salt-forming counterions, such as sodium; and/or nonionic surfactants, such as TWEEN® (ICI, Inc.; Bridgewater, N.J.), polyethylene glycol (PEG), and PLURONICS™ (BASF; Florham Park, N.J.).

Compositions containing the compound described herein or derivatives thereof suitable for parenteral injection may comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants, such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like may also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier), such as sodium citrate or dicalcium phosphate, or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They may contain opacifying agents and can also be of such composition that they release the active compound or compounds in a certain part of the intestinal tract in a delayed manner.

Examples of embedding compositions that can be used are polymeric substances and waxes. The active compounds can also be in micro-encapsulated form, if appropriate, with one or more of the above-mentioned excipients.

Liquid dosage forms for oral administration of the compounds described herein or derivatives thereof include pharmaceutically acceptable emulsions, solutions, suspensions, syrups, and elixirs. In addition to the active compounds, the liquid dosage forms may contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, may contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers, such as cocoa butter, polyethyleneglycol or a suppository wax, which are solid at ordinary temperatures but liquid at body temperature and, therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as may be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like.

These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught therein.)

Administration of the compounds and compositions described herein or pharmaceutically acceptable salts thereof can be carried out using therapeutically effective amounts of the compounds and compositions described herein or pharmaceutically acceptable salts thereof as described herein for periods of time effective to treat a disorder. The effective amount of the compounds and compositions described herein or pharmaceutically acceptable salts thereof as described herein may be determined by one of ordinary skill in the art and includes exemplary dosage amounts for a mammal of from about 0.5 to about 200 mg/kg of body weight of active compound per day, which may be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. Those of skill in the art will understand that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

III. Methods of Making the Compounds

The compounds described herein can be prepared in a variety of ways known to one skilled in the art of organic synthesis or variations thereon as appreciated by those skilled in the art. The compounds described herein can be prepared from readily available starting materials. Optimum reaction conditions may vary with the particular reactants or solvents used, but such conditions can be determined by one skilled in the art.

Variations on Formula I, Formula II, Formula III, Formula IV, Formula V, and Formula VI include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C) infrared spectroscopy, spectrophotometry (e.g., UV-visible), or mass spectrometry, or by chromatography such as high performance liquid chromatography (HPLC) or thin layer chromatography.

The compounds described by Formula I can be made, for example, according to the methods described in El-Araby et al., *Journal of Computational Chemistry*, 6(5):789-795 (2004) and International Patent Application No. WO 2005/080367. Exemplary synthetic methods are shown in Schemes 1-6:

Scheme 1: Synthesis of Compound Sd-4-1

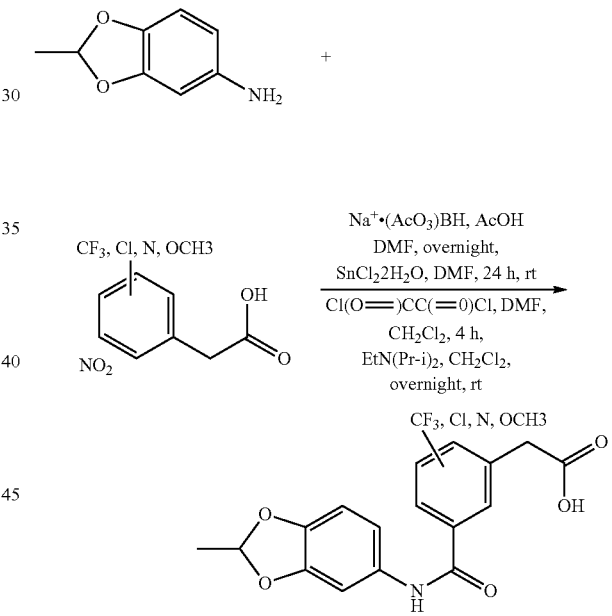

Scheme 2: Synthesis of Compound Sd-4-2

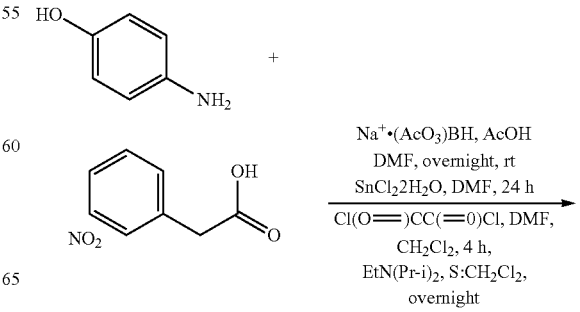

-continued

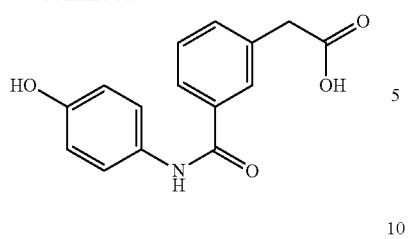

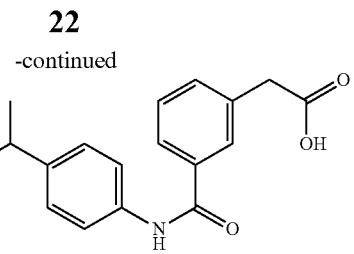

Scheme 3: Synthesis of Compound Sd-4-3

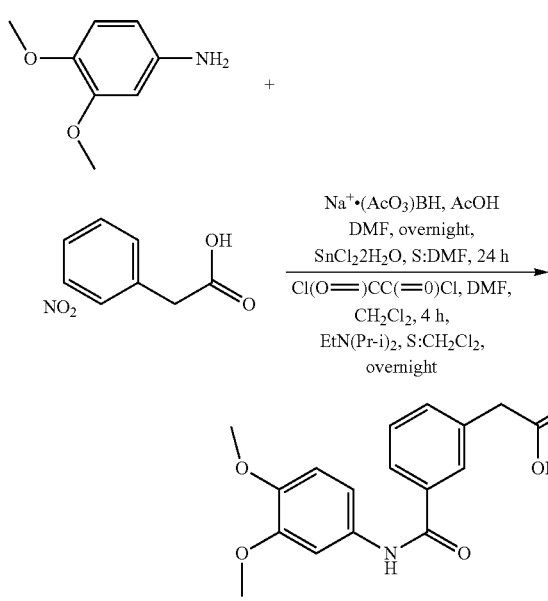

Scheme 5: Synthesis of Compound Sd-4-5

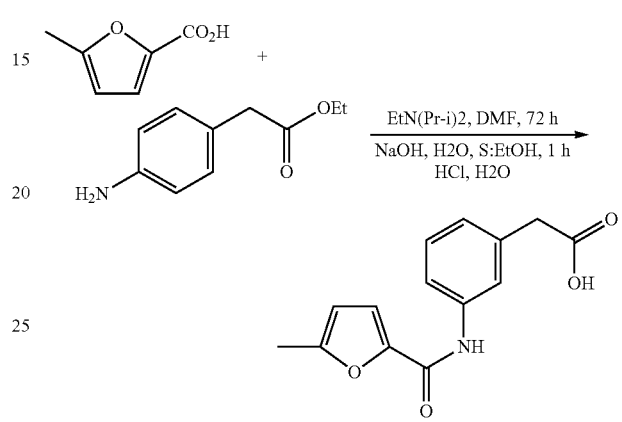

Scheme 4: Synthesis of Compound Sd-4-4

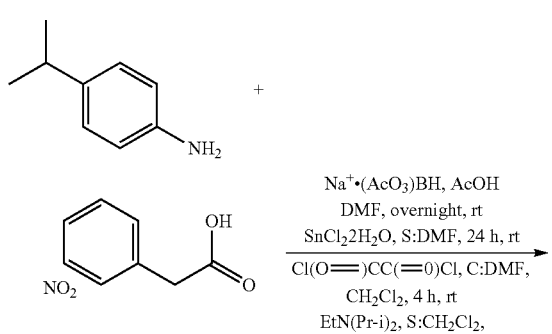

Scheme 6: Synthesis of Compound Sd-4-6

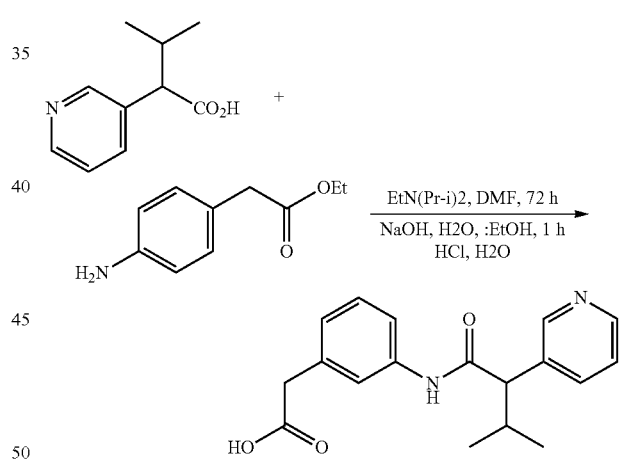

The compounds described by Formula III can be made, for example, according to the methods described in International Patent Application No. WO 2008/005651. An exemplary synthetic method is shown in Scheme 7:

Scheme 7: Synthesis of Compound Sd-5-5

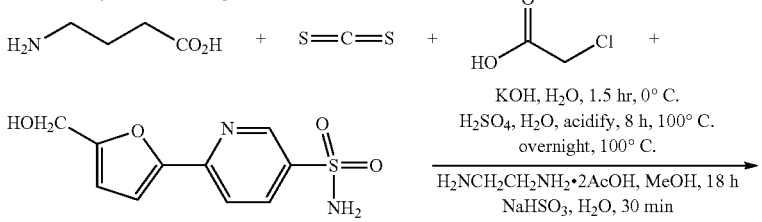

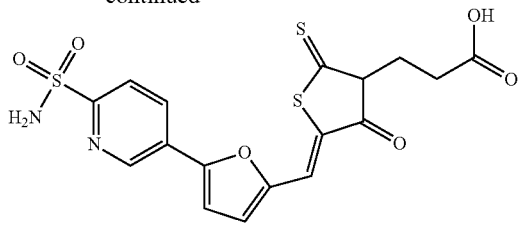

The compounds described by Formula IV can be made, for example, according to the methods described in Chen et al., *Journal of Chemical Research, Synopses,* 9:308-309 (1987). Exemplary synthetic methods are shown in Schemes 8-10:

Scheme 8: Synthesis of Compound Sd-6-1

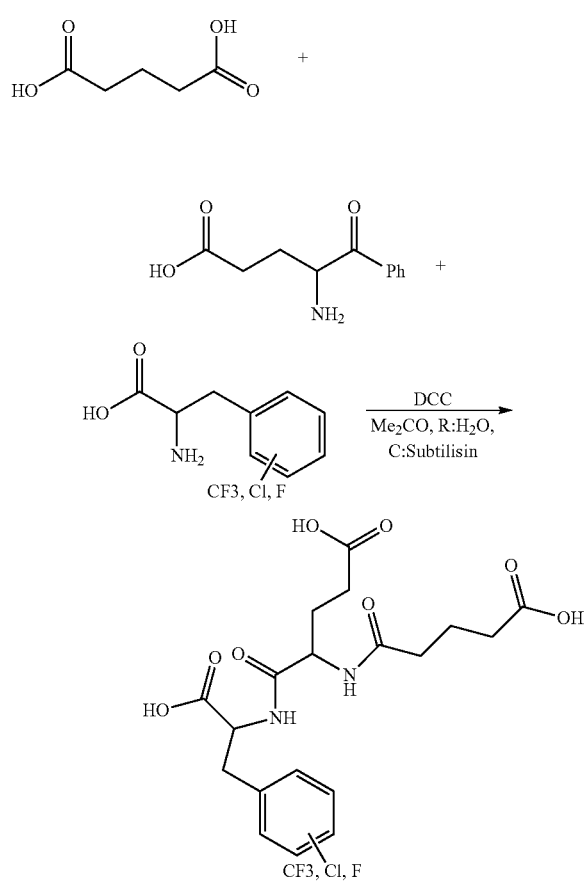

Scheme 9: Synthesis of Compound Sd-6-2

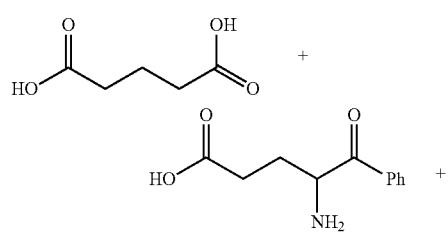

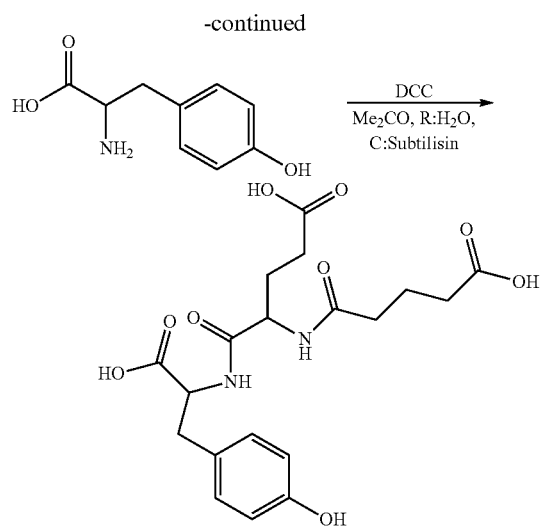

Scheme 10: Synthesis of Compound Sd-6-3

IV. Methods of Use

Provided herein are methods to treat, prevent, or ameliorate cancer and neurologic disorders in a subject. The methods include administering to a subject an effective amount of one or more of the compounds or compositions described herein, or a pharmaceutically acceptable salt or prodrug thereof. The expression "effective amount," when used to describe an amount of compound in a method, refers to the amount of a compound that achieves the desired pharmacological effect or other effect, for example, an amount that results in tumor growth rate reduction. The compounds and compositions described herein or pharmaceutically acceptable salts thereof are useful for treating cancer and neurologic disorders in humans, including, without limitation, pediatric and geriatric populations, and in animals, e.g., veterinary applications.

The method of treating or preventing cancer and neurologic disorders in a subject can further comprise administering to the subject a therapeutic agent or radiation therapy or a combination thereof. Thus, the provided compositions and methods can include one or more additional agents. The one or more additional agents and the compounds described herein or pharmaceutically acceptable salts or prodrugs thereof can be administered in any order, including concomitant, simultaneous, or sequential administration. Sequential administration can be temporally spaced order of up to several days apart. The methods can also include more than a single administration of the one or more additional agents and/or the compounds described herein or pharmaceutically acceptable salts or prodrugs thereof. The administration of the one or more additional agents and the compounds described herein or pharmaceutically acceptable salts or prodrugs thereof can be by the same or different routes and concurrently or sequentially.

Therapeutic agents include, but are not limited to, chemotherapeutic agents, anti-depressants, anxiolytics, antibodies, antivirals, steroidal and non-steroidal anti-inflammatories, conventional immunotherapeutic agents, cytokines, chemokines, and/or growth factors.

The therapeutic agent can, for example, be a chemotherapeutic agent. A chemotherapeutic agent is a compound or composition effective in inhibiting or arresting the growth of an abnormally growing cell. Thus, such an agent may be used therapeutically to treat cancer as well as other diseases marked by abnormal cell growth. Illustrative examples of chemotherapeutic compounds include, but are not limited to, bexarotene, gefitinib, erlotinib, gemcitabine, paclitaxel, docetaxel, topotecan, irinotecan, temozolomide, carmustine, vinorelbine, capecitabine, leucovorin, oxaliplatin, bevacizumab, cetuximab, panitumumab, bortezomib, oblimersen, hexamethylmelamine, ifosfamide, CPT-11, deflunomide, cycloheximide, dicarbazine, asparaginase, mitotant, vinblastine sulfate, carboplatin, colchicine, etoposide, melphalan, 6-mercaptopurine, teniposide, vinblastine, antibiotic derivatives (e.g. anthracyclines such as doxorubicin, liposomal doxorubicin, and diethylstilbestrol doxorubicin, bleomycin, daunorubicin, and dactinomycin); antiestrogens (e.g., tamoxifen); antimetabolites (e.g., fluorouracil (FU), 5-FU, methotrexate, floxuridine, interferon alpha-2B, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cisplatin, vincristine and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chlorambucil, mechlorethamine (nitrogen mustard) and thiotepa); and steroids (e.g., bethamethasone sodium phosphate).

Optionally, the therapeutic agent can be an anti-depressant. Illustrative examples of anti-depressant compounds include, but are not limited to, adatanserin hydrochloride; adinazolam; adinazolam mesylate; alaproclate; aletamine hydrochloride; amedalin hydrochloride; amitriptyline hydrochloride; amoxapine; aptazapine maleate; azaloxan fumarate; azepindole; azipramine hydrochloride; bipenamol hydrochloride; bupropion hydrochloride; butacetin; butriptyline hydrochloride; caroxazone; cartazolate; ciclazindol; cidoxepin hydrochloride; cilobamine mesylate; clodazon hydrochloride; clomipramine hydrochloride; cotinine fumarate; cyclindole; cypenamine hydrochloride; cyprolidol hydrochloride; cyproximide; daledalin tosylate; dapoxetine hydrochloride; dazadrol maleate; dazepinil hydrochloride; desipramine hydrochloride; dexamisole; deximafen; dibenzepin hydrochloride; dioxadrol hydrochloride; dothiepin hydrochloride; doxepin hydrochloride; duloxetine hydrochloride; eclanamine maleate; encyprate; etoperidone hydrochloride; fantridone hydrochloride; fehmetozole hydrochloride; fenmetramide; fezolamine fumarate; fluotracen hydrochloride; fluoxetine; fluoxetine hydrochloride; fluparoxan hydrochloride; gamfexine; guanoxyfen sulfate; imafen hydrochloride; imiloxan hydrochloride; imipramine hydrochloride; indeloxazine hydrochloride; intriptyline hydrochloride; iprindole; isocarboxazid; ketipramine fumarate; lofepramine hydrochloride; lortalamine; maprotiline; maprotiline hydrochloride; melitracen hydrochloride; milacemide hydrochloride; minaprine hydrochloride; mirtazapine; moclobemide; modaline sulfate; napactadine hydrochloride; napamezole hydrochloride; nefazodone hydrochloride; nisoxetine; nitrafudam hydrochloride; nomifensine maleate; nortriptyline hydrochloride; octriptyline phosphate; opipramol hydrochloride; oxaprotiline hydrochloride; oxypertine; paroxetine; phenelzine sulfate; pirandamine hydrochloride; pizotyline; pridefine hydrochloride; prolintane hydrochloride; protriptyline hydrochloride; quipazine maleate; rolicyprine; seproxetine hydrochloride; sertraline hydrochloride; sibutramine hydrochloride; sulpiride; suritozole; tametraline hydrochloride; tampramine fumarate; tandamine hydrochloride; thiazesim hydrochloride; thozalinone; tomoxetine hydrochloride; trazodone hydrochloride; trebenzomine hydrochloride; trimipramine; trimipramine maleate; venlafaxine hydrochloride; viloxazine hydrochloride; zimeldine hydrochloride; and zometapine.

Further, the therapeutic agent can be an anxiolytic. Illustrative examples of anxiolytic compounds include, but are not limited to, alprazolam; chlordiazepoxide; clonazepam; diazepam; lorazepam; tofisopam; buspirone; tandospirone; gepirone; barbiturates; hydroxyzine; pregbalin; chlorpheniramine; and diphenhydramine.

Any of the aforementioned therapeutic agents can be used in any combination with the compositions described herein. Combinations are administered either concomitantly (e.g., as an admixture), separately but simultaneously (e.g., via separate intravenous lines into the same subject), or sequentially (e.g., one of the compounds or agents is given first followed by the second). Thus, the term combination is used to refer to concomitant, simultaneous, or sequential administration of two or more agents.

The methods and compounds as described herein are useful for both prophylactic and therapeutic treatment. For prophylactic use, a therapeutically effective amount of the compounds and compositions or pharmaceutically acceptable salts thereof as described herein are administered to a subject prior to onset (e.g., before obvious signs of cancer or a neurologic disorder), during early onset (e.g., upon initial signs and symptoms of cancer or a neurologic disorder), or after the development of cancer or a neurologic disorder. Prophylactic administration can occur for several days to years prior to the manifestation of symptoms of cancer or a neurologic disorder. Therapeutic treatment involves administering to a subject a therapeutically effective amount of the compounds and compositions or pharmaceutically acceptable salts thereof as described herein after cancer or a neurologic disorder is diagnosed.

V. Assays

The enzymatic activity of the compounds provided herein as inhibitors of AGBL2 may be measured in standard assays, e.g., HPLC assays. Compounds that are identified as AGBL2 inhibitors are useful in treating or preventing cancer and/or neurologic disorders. Further, the compounds can be tested as inhibitors of AGBL2 in a Fluorescence Resonance Energy Transfer (FRET) assay, as described in Example 3 below. The high throughput enzyme assays and inhibitor screenings described provide real-time monitoring of the digestion process. The activities of the compounds as determined using the assays described herein can be reported in terms of $IC_{50}$. As used herein, $IC_{50}$ refers to an amount, concentration, or dosage of a particular test compound that achieves a 50% inhibition of a maximal response in an assay that measures such response.

VI. Kits

Also provided herein are kits for treating or preventing cancer or a neurologic disorder in a subject. A kit can include any of the compounds or compositions described herein. For example, a kit can include a compound of Formula I, Formula II, Formula III, Formula IV, Formula V, Formula VI, or combinations thereof. A kit can further include one or more additional agents, such as a chemotherapeutic agent (e.g., gemcitabine, paclitaxel, or tamoxifen), an anti-depressant (e.g., amitriptyline, duloxetine, or sertraline), and/or an anxiolytic (e.g., benzodiazepines, azapirones, or diphenhydramine). A kit can include an oral formulation of any of the compounds or compositions described herein. A kit can additionally include directions for use of the kit (e.g., instructions for treating a subject), a container, a means for administering the compounds or compositions, and/or a carrier.

As used herein the terms treatment, treat, or treating refer to a method of reducing one or more symptoms of a disease or condition. Thus in the disclosed method, treatment can refer to a 10%, 20%, 30%, 40%, 50%, 60%, 70%, 80%, 90%, or 100% reduction in the severity of one or more symptoms of the disease or condition. For example, a method for treating a disease is considered to be a treatment if there is a 10% reduction in one or more symptoms or signs (e.g., size of the tumor or rate of tumor growth) of the disease in a subject as compared to a control. As used herein, control refers to the untreated condition (e.g., the tumor cells not treated with the compounds and compositions described herein). Thus the reduction can be a 10%, 20%, 30%, 40%, 50%, 60%, 70%, 80%, 90%, 100%, or any percent reduction in between 10% and 100% as compared to native or control levels. It is understood that treatment does not necessarily refer to a cure or complete ablation of the disease, condition, or symptoms of the disease or condition.

As used herein, the terms prevent, preventing, and prevention of a disease or disorder refer to an action, for example, administration of a composition or therapeutic agent, that occurs before or at about the same time a subject begins to show one or more symptoms of the disease or disorder, which inhibits or delays onset or severity of one or more symptoms of the disease or disorder.

As used herein, references to decreasing, reducing, or inhibiting include a change of 10%, 20%, 30%, 40%, 50%, 60%, 70%, 80%, 90% or greater as compared to a control level. Such terms can include, but do not necessarily include, complete elimination.

As used herein, subject means both mammals and non-mammals. Mammals include, for example, humans; non-human primates, e.g., apes and monkeys; cattle; horses; sheep; rats; mice; pigs; and goats. Non-mammals include, for example, fish and birds.

Throughout this application, various publications are referenced. The disclosures of these publications in their entireties are hereby incorporated by reference into this application.

The examples below are intended to further illustrate certain aspects of the methods and compositions described herein, and are not intended to limit the scope of the claims.

EXAMPLES

Example 1

Recombinant AGBL2 and RARRES1 Quality Control

Figure 2:
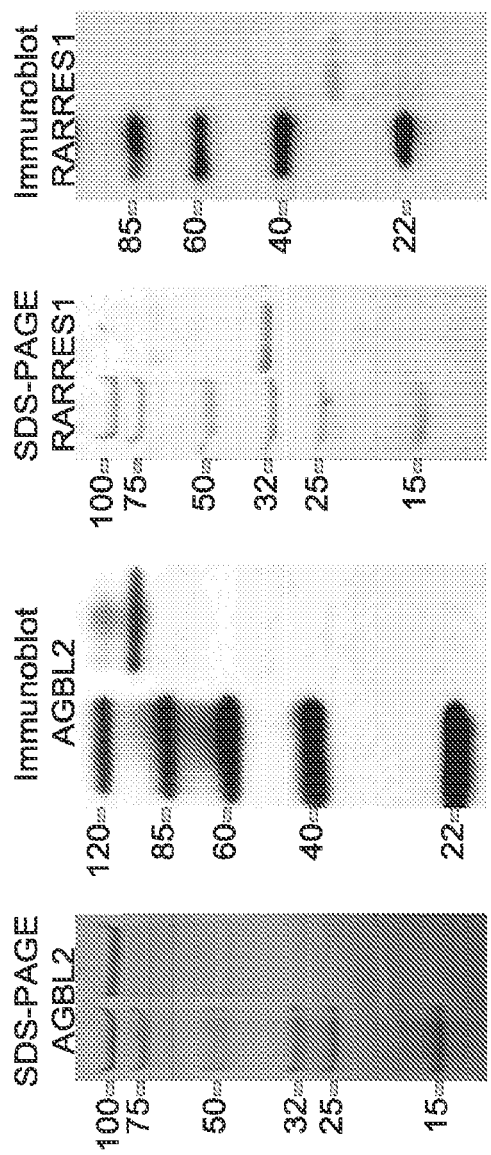
FIG. 2 shows pictures of SDS-PAGE and Immunoblots depicting the presence of RARRES1 (MW~31 kDa) and AGBL2 (MW~105 kDa).

RARRES1 or AGBL2 have significant and reciprocal effects on anoikis, anchorage, and taxol sensitivity (see FIG. 1). A high throughput fluorometric assay, using recombinant AGBL2, RARRES1, and a hydroxycoumarin-conjugated substrate, was developed to test the activity of AGBL2 candidate inhibitors. The RARRES1 and AGBL2 for use in the assays were tested for purity and quality. Specifically, N-His AGBL2 and N-His RARRES1 recombinants were obtained from inclusion bodies. In addition to confirming the gene sequence of the bacterial expressing plasmids by gene sequencing, SDS-PAGE and Western blotting were used to assess the purity and quality of the recombinant proteins. FIG. 2 shows the Coomassie Blue stained SDS gels and the immunoblots after loading 2 μg of recombinant AGBL2 (pI/MW: 9.36/105 kDa) and 1.5 μg of recombinant RARRES1 (pI/MW: 7.71/31 kDa). SDS-PAGE was run on a 4-20% gradient gel. Purity is estimated at 75% for RARRES1 and 70% for AGBL2.

Example 2

Mass Spectrometry AGBL2 Enzyme Assay

Proteins were extracted from 10 million HELA cells using RIPA buffer in the absence of enzyme inhibitors. RIPA buffer was exchanged with a 50 mM TRIS, 10 mM $CaCl_2$ pH 8.0 using a centrifugal filter device with a molecular weight cut-off of 10 kDa. AGBL2 in vitro enzymatic activity was analyzed by adding 10 μg of AGBL2 to the lysates. Lysates were separated on a 4-20% gradient SDS-PAGE gel, stained with Coomassie Blue. The band at 55 kDa representing α-tubulin was excised, destained, and digested with trypsin and proteinase K. Detyrosinated and tyrosinated C-terminal tail of α-tubulin were detected using nano liquid chromatography coupled with a quadrupole time of flight mass spectrometer (nano-LC-Q-TOF-MS). The detyrosinated to tyrosinated ratio (DTR) of tubulin increased from 1.20 (control) to 41.4 following AGBL2 overnight incubation (see FIGS. 3A and 3B).

Example 3

Tyrosination and Detyrosination of α-Tubulin

Figure 4:
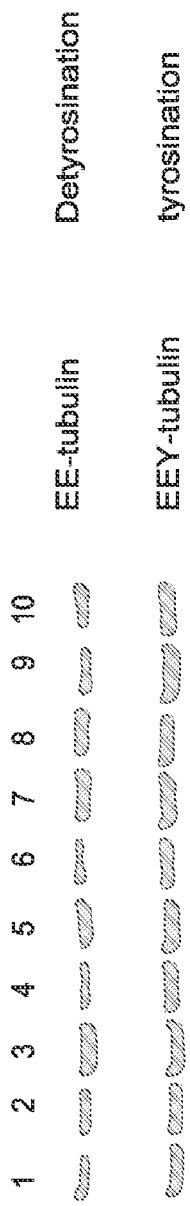
FIG. 4 shows a Western Blot depicting tyrosinated and detyrosinated α-tubulin in HEK 293 cells and HEK 293 cells expressing TIG1. Row 1 represents the control (EV), row 2 represents overexpressed TIG1, row 3 represents EV and compound Sd-1, row 4 represents TIG1 and compound Sd-1, row 5 represents EV and compound Sd-2, row 6 represents TIG1 and compound Sd-2, row 7 represents EV and compound Sd-3, row 8 represents TIG1 and compound Sd-3, row 9 represents EV and compound Sd-4, and row 10 represents TIG1 and compound Sd-4.

HEK 293 and HEK 293 stably expressing TIG1 (HEK293-TIG1) were grown in DMEM supplemented with 10% FBS. Cells (200 K) were seeded in 6-well plate dishes. The HEK293 media was changed 24 hrs post-seeding with a media containing one of Sd-1, Sd-2, Sd-3, or Sd-4 at a concentration of 1 microM. Cells were lysed after 2 hrs and Western blotting was performed against the tyrosinated and detyrosinated α-tubulin in the sample. The results are shown in FIG. 4. FIG. 4, row 1 represents the control (EV), row 2 represents overexpressed TIG1, row 3 represents EV and compound Sd-1, row 4 represents TIG1 and compound Sd-1, row 5 represents EV and compound Sd-2, row 6 represents TIG1 and compound Sd-2, row 7 represents EV and compound Sd-3, row 8 represents TIG1 and compound Sd-3, row 9 represents EV and compound Sd-4, and row 10 represents TIG1 and compound Sd-4.

Example 4

High Throughput Enzyme Kinetic Assay

Figure 5:
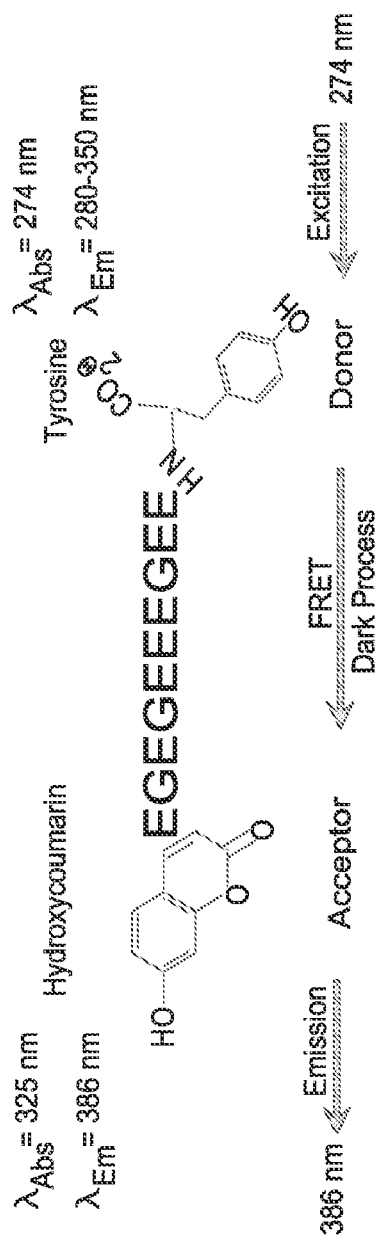
FIG. 5 shows a scheme of a high-throughput enzyme assay.

Fluorescence Resonance Energy Transfer (FRET) principle can be applied to generate real-time enzymatic activity data. The tyrosinated C-terminal tail of tubulin has a tyrosine at the C-terminal. Tyrosines absorb at 270 nm and emit in the 280 to 350 nm range with a $\lambda_{Max}$=303 nm. Adding a hydroxycoumarin that absorbs in the range of 300 to 350 nm to the N-terminal of the CTT of tubulin (see FIG. 5) allows the quenching of the tyrosine emission that can be monitored at 303 nm. Emissions at 303 nm can be detected after the cleavage of the tyrosine residue since the latter will follow a Brownian motion and become physical situated far from the quencher (Hydroxycoumarin). Assays can be performed at 25° C. in 10 mM $CaCl_2$, 0.2 M NaCl, and 0.05% Brij-35 in 50 mM HEPES, pH 7.5, over a substrate concentration range of 1-5 mM and an enzyme concentration range of 0.1-50 nM. An exemplary assay was performed by incubating 186 μL of buffer solution, 4 μL of substrate solution, and then adding 10 μL of AGBL2 solution. The mixture was then incubated for 15 to 120 minutes at 25° C.

Figure 6:
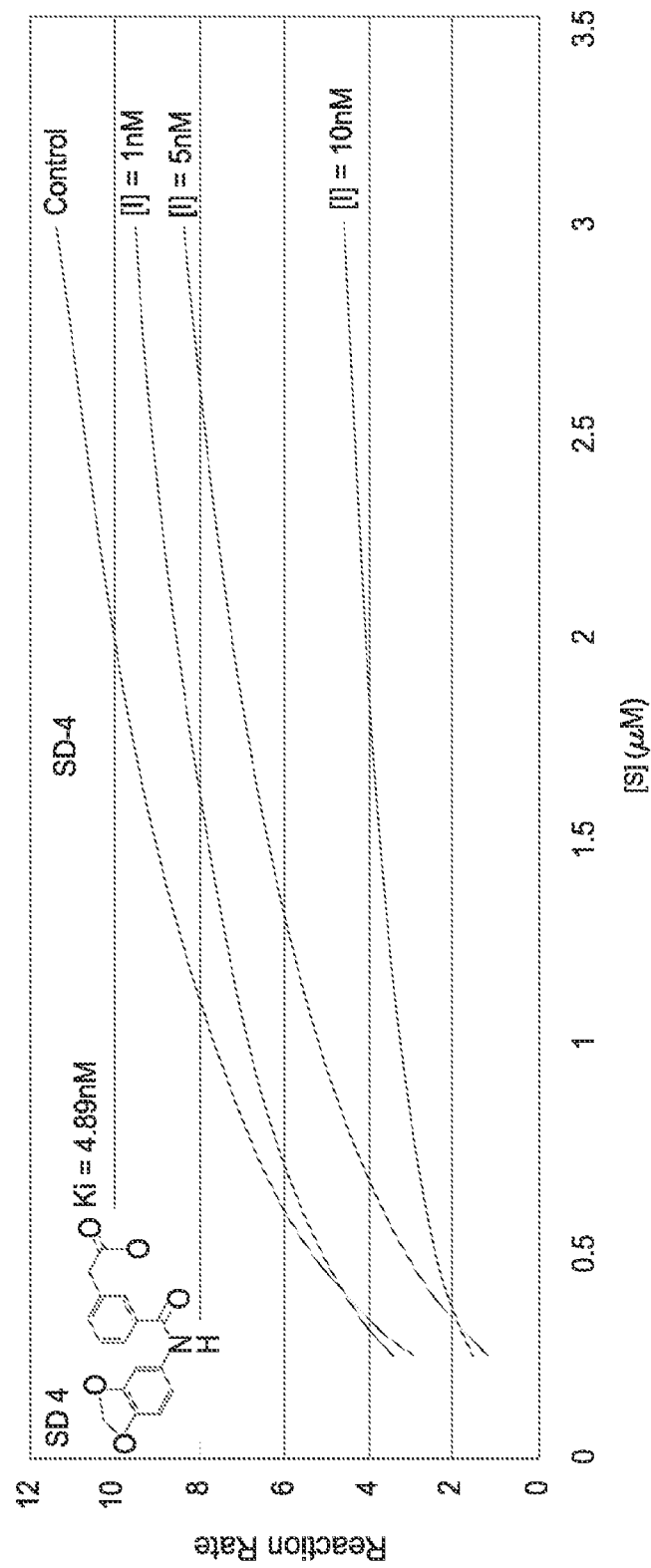
FIG. 6 is a graph demonstrating the inhibition of AGBL2 activity (1 nM) by compound Sd-4 at varying substrate concentrations.

The reaction rate can be analyzed using different substrate concentrations and the saturation curve can be drawn. The maximum reaction rate ($V_{max}$) and the substrate concentration at half the $V_{max}$ referred to as the Michaelis-Menten constant ($K_M$) can be determined from the saturation curve. Inhibitors can also be analyzed and a saturation curve in the presence of inhibitor can be drawn. Compound Sd-4 (1 nM, 5 nM, and 10 nM) was analyzed according to this method, as shown in FIG. 6. The reaction rate was analyzed using substrate concentrations over a range of 0 to 3 μM. The Michaelis-Menten constant in the presence of inhibitor referred to as $K_{M, Observed}$ can be similarly obtained from the saturation curve. The dissociation constant of the inhibitor ($K_i$) can be calculated using the following equation: $K_i$=[Inhibitor]/(($K_{M,obs}/K_M$)−1.0).

Example 5

Enzyme Inhibition Kinetic Assays

Kinetic assays of the inhibition of AGBL2 were carried out using the substrate described in Example 4 to measure inhibition constants. Enzymatic assays were performed at 25° C. in 50 mM HEPES buffer at pH 7.5 in the presence of 10 mM $CaCl_2$, 0.2 M NaCl, and 0.01% or 0.05% Brij-35 with substrate concentrations of 1 μM. The release of tyrosine was monitored by measuring fluorescence (excitation and emission wavelengths of 270 nm and 303 nm, respectively). The compounds tested as inhibitors included compound Sd-1, compound Sd-2, compound Sd-3, and compound Sd-4. All stock solutions of inhibitors were in methanol. For inhibition assays, 10 μL of inhibitor stock solution, 176 μL of assay buffer, and 10 μL of enzyme stock solution were mixed and incubated for 30 to 60 minutes prior to initiation of the assay, which was accomplished by adding and mixing 4 μL of substrate stock solution. Enzyme concentrations ranged from 0.2 to 7 nM during the assay. Apparent inhibition constant ($K_i^{app}$) values were calculated by fitting the kinetics data to the Morrison equation for tight-binding inhibitors, where $v_i$ and $v_o$ are the initial rates with and without inhibitor, respectively, and $[E]_o$ and $[I]_o$ are the initial (total) enzyme and inhibitor concentrations, respectively. The Ki values of the four tested compounds and of recombinant RARRES1, all including 1 nM of recombinant AGBL2) are shown in Table 1.

TABLE 1

| Inhibitor | Ki (nM) |
| --- | --- |
| Sd-1 | 173 |
| Sd-2 | 87 |
| Sd-3 | 428 |
| Sd-4 | 4.89 |
| RARRES1 | 27 |

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus, a combination of steps, elements, components, or constituents may be explicitly mentioned herein; however, all other combinations of steps, elements, components, and constituents are included, even though not explicitly stated.

What is claimed is:

1. A method of treating cancer in a subject, comprising:
administering to the subject an effective amount of one or more compounds of the following structure:

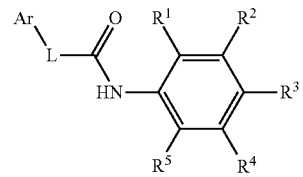

or a pharmaceutically acceptable salt thereof, wherein:
Ar is

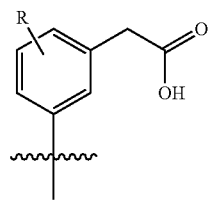

wherein R is trifluoromethyl, chloro, fluoro, methoxy, amino, or nitro;
L is absent;
$R^1$, $R^4$, and $R^5$ are each independently selected from the group consisting of hydrogen, halogen, hydroxyl, cyano, nitro, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, and substituted or unsubstituted carboxyl; and
$R^2$ and $R^3$ are each independently selected from the group consisting of hydrogen, halogen, hydroxyl, cyano, nitro, substituted or unsubstituted alkyl, substituted or unsubstituted heteroalkyl, substituted or unsubstituted amino, substituted or unsubstituted aryl, substituted or unsubstituted heteroaryl, substituted or unsubstituted alkoxyl, substituted or unsubstituted aryloxyl, substituted or unsubstituted carbonyl, or substituted or unsubstituted carboxyl, or $R^2$ and $R^3$ combine to form a substituted or unsubstituted heterocycloalkyl, or a composition comprising the compound and a pharmaceutically acceptable carrier.

2. The method of claim 1, further comprising administering a second therapeutic agent to the subject.

3. The method of claim 2, wherein the second therapeutic agent is a chemotherapeutic agent.

4. The method of claim 1, wherein $R^2$ and $R^3$ combine to form a substituted or unsubstituted heterocycloalkyl.

5. The method of claim 1, wherein Ar is

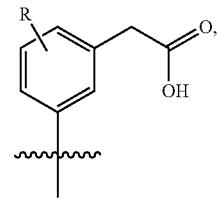

wherein R is trifluoromethyl, chloro, fluoro, methoxy, amino, or nitro.

6. The method of claim 1, wherein the compound is

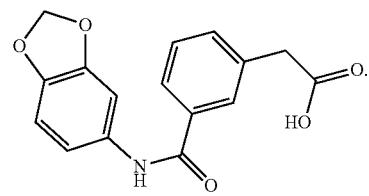 [SMILES: O=C(O)Cc1cccc(C(=O)Nc2ccc3c(c2)OCO3)c1]

\* \* \* \* \*